(12) United States Patent
Lubard et al.

(10) Patent No.: US 7,831,061 B1
(45) Date of Patent: Nov. 9, 2010

(54) NONINVASIVE POLYGRAPH TECHNOLOGY BASED ON OPTICAL ANALYSIS

(75) Inventors: Stephen C. Lubard, Woodland Hills, CA (US); J. Jerome Holton, Alexandria, VA (US)

(73) Assignee: Defense Group, Inc., Falls Church, VA (US)

( * ) Notice: Subject to any disclaimer, the term of this patent is extended or adjusted under 35 U.S.C. 154(b) by 0 days.

(21) Appl. No.: 12/313,743

(22) Filed: Nov. 24, 2008

Related U.S. Application Data

(63) Continuation-in-part of application No. 10/324,000, filed on Dec. 20, 2002, now abandoned.

(60) Provisional application No. 60/344,703, filed on Dec. 24, 2001.

(51) Int. Cl.
*G06K 9/00* (2006.01)

(52) U.S. Cl. ..................... 382/100

(58) Field of Classification Search ............. 382/100
See application file for complete search history.

(56) References Cited

U.S. PATENT DOCUMENTS

| | | | |
|---|---|---|---|
| 2,944,542 A | 7/1960 | Barnett et al. | |
| 3,230,951 A | 1/1966 | Teschner | |
| 4,085,740 A | 4/1978 | Allen, Jr. | |
| 4,123,160 A | 10/1978 | Caputo et al. | |
| 4,289,142 A | 9/1981 | Kearns | |
| RE33,865 E | 3/1992 | Knight et al. | |
| 5,142,372 A | 8/1992 | Alfano et al. | |
| 5,241,360 A | 8/1993 | Key et al. | |
| 5,278,403 A * | 1/1994 | Alfano et al. | 250/214 VT |
| 5,467,122 A * | 11/1995 | Bowker et al. | 348/31 |
| 5,507,291 A * | 4/1996 | Stirbl et al. | 600/407 |
| 5,792,049 A | 8/1998 | Eppstein et al. | |
| 5,892,575 A | 4/1999 | Marino | |
| 6,062,216 A * | 5/2000 | Corn | 128/204.23 |
| 6,339,715 B1 | 1/2002 | Bahr et al. | |
| 6,873,716 B1 * | 3/2005 | Bowker et al. | 382/128 |
| 2004/0031906 A1 | 2/2004 | Gleckler | |

OTHER PUBLICATIONS

Lee, et al., "LIDAR Measurement of Water Temperature by Using Frequency-Shifted Raman Scattering", Journal of the Korean Physical Society, vol. 38, No. 6, Jun. 2001, pp. 659-665.

* cited by examiner

*Primary Examiner*—Wenpeng Chen
(74) *Attorney, Agent, or Firm*—Peter I. Lippman

(57) ABSTRACT

A system and method for unobtrusively and noninvasively subjecting a living subject to tests for the purpose of determining whether that subject is truthful or is under stress, or both. A series of radiation pulses, preferably infrared laser pulses, is directed by a lidar transceiver toward the subject—which returns (e.g. reflects or scatters) the pulses back to the transceiver, which time-resolves that return to segregate and isolate phenomena at, within or in front of the subject's skin. The transceiver is connected to an information processing device capable of determining various physiological characteristics exhibited by the subject in these several regions, respectively. A display associated with the processor visually indicates these physiological characteristics.

19 Claims, 9 Drawing Sheets

NONINVASIVE POLYGRAPH TECHNOLOGY BASED ON OPTICAL ANALYSIS

This is a continuation-in-part of our application Ser. No. 10/324,000 filed on Dec. 20, 2002 now abandoned and thereby its precursor provisional application 60/344,703 filed on Dec. 24, 2001—both wholly incorporated herein. Priority benefit of both these filings is hereby asserted.

BACKGROUND

1. Field of the Invention

This invention relates generally to polygraph systems and methods; and more particularly to such apparatus or procedures that require no mechanical contact with the subject.

2. Nomenclature

Defining the bounds of this invention calls for clear understanding of relationships between these two discrete concepts:

"frequency shift" (or "frequency change", or "change of frequency") of a carrier of pulses; and "change in frequency characteristics" (or "frequency band change", or "change of bandwidth") of such a carrier.

These relationships are taken up in this subsection 2.

In patent matters it has long been recognized by the High Courts that a patent applicant "is entitled to be his own lexicographer". This means, of course, that an inventor is permitted to define terms, for purposes of his application (and resulting patent if any) as the inventor prefers. Modern appellate decisions have extended this rule, even so far as to permit an applicant to define terms in ways that diverge from and indeed are even contrary to standard accepted meanings.

For purposes of this document, the phrase "frequency shift" (or "change") shall be understood to encompass "change in frequency characteristics" (including e.g. "change of bandwidth")—except where expressly otherwise indicated in the text (and except in this subsection "2. NOMENCLATURE" of this "BACKGROUND" section). Thus for example the concept of a frequency shift shall be understood to mean (a) literally, a change or shift in frequency as such, or (b) a change in bandwidth or other change in frequency characteristics, or (c) both.

This definition of "frequency shift" (or "frequency change") conforms the language in this document to casual, informal jargon used by many scientists, engineers and technicians in this field. Such casual but ubiquitous usage, though possibly less than completely rigorous, was in fact part of the origin of language in certain of the appended claims, in this and the parent patent application. Hence this definition is consistent both with usage and (more importantly) with original concepts taught in the parent case.

In this document, wherever it is intended to isolate the concept of a shift in frequency, without encompassing any other sort of change in frequency characteristics, the text of this document recites either e.g. "frequency shift per se" or "frequency shift, literally".

Also for purposes of this document the terms "scattering" or "backscattering"—both very generally synonymous with "return"—apply both to in-band return, at the same wavelength as is transmitted, and to Raman return at a different wavelength.

3. Related Art

The art of the popularly designated "lie detector" is a mature one and well known. In it, ordinarily a subject to be interrogated is attached to various sensors for measurement of heart rate, breathing rate, perhaps skin characteristics and body temperature, and sometimes other body parameters. This technology is generally effective and a helpful tool, although the legal system has been traditionally somewhat slow to accept it because of recognized susceptibility to both false positive results (i.e. incorrect apparent finding of a lie when the subject has actually been truthful) and false negative results (i.e. failure to detect an actual lie, or in other words an incorrect finding of truthfulness).

Polygraph testing and recording is either accompanied by or part of an interrogation of some kind, and in turn commonly accompanied by audio and sometimes video recording. Thus, to conduct a full examination, operation of the recording polygraph devices themselves is additive with respect to, for instance, a video camera with a sound track.

A drawback in conventional polygraphy is the need to attach the sensors before the examination and detach them afterward. Aside from the awkwardness of this procedure and the time consumed, some subjects are uncooperative or violent and may be dangerous to the operators of the equipment—while others may pose a hazard by virtue of highly communicable diseases such as AIDS, hepatitis and ebola.

Another difficulty with the conventional technology is the relatively high incidence of false positives due to a subject's nervousness about being connected to the apparatus and then questioned. A less-obtrusive system could significantly mitigate this problem.

Also it is well known that some subjects are able to suppress bodily response to stress (leading to false negatives), and others can generate voluntary variations and correlations (leading to a continuing stream of false positives) that mask response to stress. In effect the subject is lying not only to the questioner but to the machine as well.

The problem of unwitting false positives also is complicated by the problem of intentional false positives. These various effects degrade the reliability of all conventional polygraphic systems and techniques.

Not all polygraphy is related to criminal testimony. Some is potentially useful instead in hiring applicants for sensitive jobs such as intelligence, police and other security work—or even simply positions calling for a high degree of personal stability and trustworthiness, as for instance teachers, managers, pilots, bus drivers, medical and paramedical workers, and mass-transportation maintenance personnel.

In these areas it is unseemly to subject applicants to the indignity of attaching leads and sensors to the skin. In common situations where only one polygrapher is available, an additional issue of sexual impropriety or at least offensiveness may arise when a subject and a polygrapher are of opposite gender.

Also related to the characteristics of a polygrapher is the requirement for attention by a professional who is highly trained. A more highly automated system could reduce or eliminate the need for such advanced expertise—particularly if resulting primary data, without need for interpretation, could be used directly as evidence.

Results from conventional polygraphy do not appear to be sufficiently consistent for such use. This field accordingly would benefit from refinement of the technology to provide more reproducible results from test to test.

Finally, in most cases observation of a subject's body parameters is subject to considerations of civil liberties and personal privacy under the United States Constitution—and similar established policy worldwide; nevertheless, there are established circumstances under which such considerations are inapplicable or at least very severely attenuated. For example, it is understood that the law in much if not all of the United States accords to convicted felons while in prison a much lower degree of personal privacy than to citizens generally. Therefore it would be appropriate and desirable in such circumstances to have some means for monitoring vital signs without a subject's knowledge.

Accordingly it would be desirable to provide a form of polygraphic equipment and methodology requiring no such sensor attachment, and also amenable to a wider range of vital parameters through a single sensor module.

A heretofore-unrelated art is that of light detection and ranging—sometimes called "lidar" by analogy to radio detection and ranging, and its better-known acronym "radar". Most conspicuously lidar has been used in large-scale aerial imaging, as in U.S. Pat. No. 5,467,122 of Bowker et al. directed to a streak-tube form of lidar for ocean-volume monitoring; but small- and even medical-scale applications are known as set forth in a related patent application of the same inventors, and to uses at a wide range of scales as disclosed in international application WO 97/18487 of Bowker et al.

The references just cited generally use a translating or scanning pulse source, with the receiver and transmitter substantially collocated. Through use of a streak-tube time resolver, they intrinsically map distance ("range"), between the transceiver and objects of interest, into position along one dimension (e.g. height) of a display screen—so that each pulse provides a sectional, two-dimensional image in a plane passing through the transceiver.

Due to the scanning or translation of the transceiver, successive pulses provide substantially parallel such individual sectional images. These can then be integrated visually or otherwise into, effectively, a three-dimensional image.

Another well-known form of streak-tube lidar avoids the translation of the transceiver, substituting a different kind of remapping by use of a fiber-optic prism with rows of fiber-optic pixels physically rearranged—so that an entire two-dimensional image can be presented to a streak tube as a single line (i.e. one-dimensional) image. The streak tube is then able to time-resolve motion within the entire image, based on a single laser pulse; but a computer reassembly of the image—with its motion—is required since an image would otherwise appear unintelligibly scrambled by the original action of the fiber remapper.

This technology is epitomized by well-known seminal patents of Knight and of Alfano. No fiber-optic remapper is needed in the scanning-transceiver systems; but the latter can acquire with a single laser pulse only a very small section of an entire three-dimensional image, whereas the remapper enables collection of an entire such image from each pulse.

In still another variant, sometimes called a "bistatic" configuration, the lidar transmitter and receiver are not collocated but rather are in quite different locations. Here the laser pulses reflected from a subject are distorted by the effectively ellipsoidal character of the wavefronts reaching the receiver.

Here too, a computer reconstruction of the image is needed if the application at hand calls for a natural-appearing picture. Bistatic streak-tube lidar configurations are analogous to the similarly separated source/receiver configuration of radar systems.

A streak tube, however, is only one example of devices suited for time-resolution in lidar systems. Other alternatives will be introduced later in this document.

These several forms of lidar have been used to measure the conformation of land, or other objects, either directly in view or through turbid media that obscure direct vision. To the best of our knowledge no connection has ever been suggested between lidar and polygraphy.

The three patent documents mentioned above, and all references cited therein, are wholly incorporated by reference into the present document. In particular this incorporation by reference shall include but not be limited to pictorial illustrations in those documents, which accordingly shall be regarded as directly presented in the present document.

As can now be seen, the related polygraphic art remains subject to significant problems, and the efforts outlined above—although praiseworthy—have left room for considerable refinement.

SUMMARY OF THE DISCLOSURE

The present invention provides just such refinement. In its preferred embodiments the invention has several independent aspects or facets—which in general can, however, be used together in combination to advantage.

In preferred embodiments of its first major independent facet or aspect, the invention is a system for noninvasively conducting polygraphic tests for determining the existence of stress on a living subject. The system includes a lidar radiation transmitter provided at a distance from the subject for transmitting a plurality of coherent lidar radiation pulses, in a particular optical frequency band that serves as a lidar data carrier, directed toward the subject.

The system of this first main aspect or facet also includes a lidar receiver, provided at a distance from the subject, for receiving the lidar pulses returned from the subject. Between said transmitted and received pulses, respectively, there is a variable time delay that is associated with variable distances between the subject and the transmitter and receiver.

The received pulses with variable delay contain information relating to a plurality of physiological characteristics of the subject. These characteristics in turn are indicative of stress of the subject.

The system also includes some means for time-resolving each received pulse to analyze the delay and thereby the variable distances. Further included is an information-processing device, in communication with the receiver, for processing the variable time delay.

The foregoing may represent a description or definition of the first aspect or facet of the invention in its broadest or most general form. Even as couched in these broad terms, however, it can be seen that this facet of the invention importantly advances the art.

In particular, as will be seen in great detail from this document, by virtue of exploiting time-delay differences to analyze variable distances between the lidar transceiver and the subject, the apparatus of this facet of the invention is able to assess the state of the subject very objectively. The subject's state in turn is very readily interpreted in terms of polygraphy, but to a much finer degree—and, once again, without touching the subject or attaching any electrical leads or contacts.

Although the first major aspect of the invention thus significantly advances the art, nevertheless to optimize enjoyment of its benefits preferably the invention is practiced in conjunction with certain additional features or characteristics. In particular, preferably the lidar receiver includes some means for measuring frequency shifts in the carrier of said received pulses. Such shifts are a measure of the temperature of the subject.

This basic preference is the first of a series of preferences that are, in effect, nested: if this first preference is satisfied, then a further subpreference is that the information-processing device also interpret the measured frequency shifts to determine the temperature of the subject. In this case a yet-further "subsubpreference" is that the time-resolving means include some means for determining relative distance from the transmitter to the subject and thence to said receiver.

Given the nested preferences stated above, then it is yet-further preferable that the information-processing device utilize a fast Fourier transform of a series of returned radiation pulses. The transform is used to measure respiration rate or heart rate, or both, of the subject.

Another basic preference is that the system further include a display device for displaying an output of the plurality of physiological characteristics. If such a display device is provided, then three additional subpreferences come into play: it is preferred that the plurality of characteristics displayed include at least one of the subject's respiration rate and heart rate, in addition to said temperature. It is also preferred that the information-processing device combine the plurality of physiological characteristics to produce a further single output, displayed on the display device, indicative of the truthfulness of the subject.

The third subpreference is somewhat more complex. Here it is preferred that the plurality of physiological characteristics include:

the subject's perspiration, or salinity on or in the subject, or both perspiration and said salinity; and At the same time it is preferred that the information-processing device includes a spectral analysis device for determining (1) the existence and degree of perspiration on the subject's body, and (2) the existence and magnitude of salinity on or in the subject, or (3) both.

if this third subpreference is observed, then a yet-further subsubpreference is that the information-processing device measure changes in amplitude, versus time, of the reflected pulses—to measure perspiration of the subject.

Four additional basic preferences will be stated next. First, it is preferred that the transmitter include some means for transmitting the plurality of lidar pulses as a substantially unitary single sequence of multiple lidar pulses; and that the substantially unitary single sequence of lidar pulses generates data indicative of substantially all of said plurality of physiological characteristics.

A second of the four is that the said transmitter produces a plurality of lidar radiation pulses that are progressively shifted over at least a portion of the subject's body. People skilled in this field will recognize this arrangement as a "push-broom" type of lidar system.

A third of the four additional basic preferences is that the transmitter produces a plurality of lidar pulses, all of which are directed toward the subject's body; and the said information-processing device includes an image remapper. People skilled in this field will recognize this as, very generally, a Knight/Alfano fiber-optic-remapper type of lidar system.

The last of the four additional basic preferences under discussion is that the receiver in general receives lidar pulses returned from: (1) within the subject's body, and (2) gas or vapor if present outside the subject's body, as well as (3) the surface of the subject's body. Here the information-processing device includes some means for applying the processed variable time delay to discriminate among these three types of received return, and some means for applying different algorithms to analyze the three types of return, respectively.

In preferred embodiments of its second major independent facet or aspect, the invention is a method for noninvasively conducting polygraphic tests for assessing existence or degree of stress on a living subject. The method includes the step of producing a substantially single, unitary series of coherent lidar-radiation pulses, from a lidar transmitter that is at a distance from the subject.

Another step is transmitting the series of coherent radiation pulses toward the subject. Still another step is receiving the substantially single, unitary series of lidar pulses, returned from the subject, by a receiver that is at a distance from the subject—the received pulses including, relative to the transmitted pulses, a measurable frequency shift.

Yet another step is analyzing the measurable frequency shift. This analysis is to determine various physiological characteristics of the subject that are indicative of the subject's stress.

In this method of the second main aspect or facet of the invention, substantially all of the various physical characteristics are determined from the substantially single, unitary series of lidar pulses. Also in this method the receiving step includes receiving lidar pulses of different types, namely returned at least from (1) within the subject's body, and (2) the surface of the subject's body. Here the analyzing step includes applying information about arrival times of the received lidar pulses to discriminate among different types of received return, and applying different algorithms for analyzing the different types of received return, respectively.

The foregoing may represent a description or definition of the second aspect or facet of the invention in its broadest or most general form. Even as couched in these broad terms, however, it can be seen that this facet of the invention importantly advances the art.

In particular, inclusion of a frequency shift opens the way to several extremely powerful analytical techniques for extracting information about the living subject. It is believed that no such capability is found in the prior art.

The frequency shift itself can be literally a change in frequency, or can be a change in other frequency characteristics (e.g. bandwidth) of the transmitted pulses. Most particularly the frequency shift can be used in fluorescence analysis, or in Raman analysis—as discussed in greater detail elsewhere in this document.

Thus frequency-shift analysis very greatly enlarges ability of the present invention to enlist these extremely sophisticated measurement regimes in polygraphy. Once again, if desired this can be accomplished without any awareness by the subject that any instrumented analysis is taking place. It will shortly be seen that this kind of analysis enormously expands the capacity of the present invention to detect and assess subject stress, truthfulness, health factors, and other phenomena.

Although the second major aspect of the invention thus significantly advances the art, nevertheless to optimize enjoyment of its benefits preferably the invention is practiced in conjunction with certain additional features or characteristics. In particular, preferably the method further includes the step of interrogating the human subject during the producing, transmitting and receiving steps. In addition preferably the receiving step further includes receiving lidar pulses returned from gas or vapor if present outside the subject's body.

In preferred embodiments of its third major independent facet or aspect, the invention is a system for noninvasively conducting polygraphic tests to determine existence of stress on a living subject. The system includes a lidar transmitter at a distance from the subject for transmitting a plurality of coherent lidar pulses, in a particular frequency band that serves as a lidar-data carrier, directed toward the subject.

Also included is a lidar receiver at a distance from the subject for receiving pulses returned from the subject. Between the transmitted and received pulses, respectively, there is at least one measurable frequency shift in the carrier. The at least one measurable frequency shift contains information relating to plural physiological characteristics, of the living subject, indicative of stress of the subject.

The system also includes some means for time-resolving each received pulse. These means, in turn, include some means for measuring frequency shifts in the carrier of the received pulses. These shifts are a measure of the temperature of the subject.

Also included in the apparatus is an information-processing device in communication with the receiver for processing the at least one measurable frequency shift.

The foregoing may represent a description or definition of the third aspect or facet of the invention in its broadest or most general form. Even as couched in these broad terms, however, it can be seen that this facet of the invention importantly advances the art.

In particular, this apparatus aspect of the invention includes frequency-shift measurement. Accordingly this third facet of the invention may be seen as an apparatus variant of the second, method aspect—having essentially the same benefits as that second aspect—but with express application to measurement of the subject's temperature.

Although the third major aspect of the invention thus significantly advances the art, nevertheless to optimize enjoyment of its benefits preferably the invention is practiced in conjunction with certain additional features or characteristics. In particular, a basic preference is that the received pulses further include, relative to the transmitted pulses, a variable time delay relative to the transmitted pulses—as in the previously discussed first main aspect of the invention. In addition the receiver further includes some means for analyzing the time delay, to determine at least one physiological characteristic of the subject which is indicative of stress of the subject or truthfulness of the subject, or both.

If this first time-delay preference is observed, then it is further preferred that the lidar transmitter include plural laser emitters operating at respective frequencies. These frequencies are at least slightly different from one another. The plural laser emitters are directed toward respective points of the subject's body.

In this case the receiving means in general include some means for receiving pulses of different types, namely pulses returned at least from (1) within the subject's body, and from (2) the surface of the subject's body. The analyzing means include some means for applying the analyzed variable time delay to discriminate between or among different types of received return, and for applying different algorithms to analyze the different types of return, respectively.

If the preference for plural lasers is observed, then a further preference is that the targeted points of the subject's body are at least slightly different from one another. Here the receiving means further include some means for receiving pulses due to the plural laser emitters, respectively, and for receiving pulses of a third type, namely pulses returned from gas or vapor if present outside the subject's body. Also in this case the analyzing means include some means for applying a further different algorithm to analyze the third type of return. This form of the invention derives respective information from pulses received due to the plural laser emitters, and furthermore combines information derived from received pulses due to the plural laser emitters, respectively, to generate enhanced information.

By selectively and carefully combining information due to plural and even multiple emitters, forms of the present invention can very greatly improve signal-to-noise ratio in important kinds of measurements—particularly but by no means limited to Raman-based analysis of temperature.

Primarily for definiteness, in the foregoing discussion, considerable structure has been described as among the several aspects of the invention and their various preferences, subpreferences etc. More generally as noted earlier all the different facets or aspects of the invention are capable of practice in combinations together, and most of the preferences mentioned in the discussion above are usable in any or all of the defined aspects. That is, the preferences are not usable only with the aspects with which they are expressly associated, and not only within the preference structures mentioned, in the above text.

The foregoing principles and advantages of the invention will be more clearly understood and appreciated from the following description of preferred embodiments—and related illustrations, of which:

DETAILED DESCRIPTION OF THE PREFERRED EMBODIMENTS

Preferred embodiments of the invention provide a remote (i.e. noncontact) and if desired clandestine technique and apparatus for lie-detector tests, using analysis of three-dimensional lidar data. Such data are obtained by, for example, a range-gated electrooptical lidar camera system acquiring image-data frames at roughly 10 to 200 Hz (more preferably near the high end of this laser-pulse-rate range) over a relatively small area, in a generally continuous way with a pulsed laser source.

The "small area" just mentioned is most-typically the face and upper chest area of the subject. The present invention, however, is not so limited.

As will be seen, frame rate may depend very strongly on which of the above-outlined types of lidar system is in use. A scanning system is simpler in terms of hardware but also much slower in terms of overall three-dimensional frame rate.

This kind of apparatus is able to acquire a great range of vital signs—including but not limited to sweating (and, if so, salinity or other chemical details of the sweat), body temperature, heart rate, breathing rate, shivering or eye-blinking rate, and other parameters appropriate to monitoring of probable truthfulness in a subject.

Exploitation of lidar ranging—Capabilities of the invention are particularly powerful because of its capacity for resolving different return signals arising at very slightly different distances from the lidar transceiver apparatus. In the present invention these different return signals are made to represent phenomena in corresponding different zones of the human (or other) subject's body—what may be called "depth zones".

The phrase "depth zones" here refers to extremely shallow volumes among which the apparatus is able to discriminate. The term "shallow" here means shallow along the direction of the propagating beam from, and the radiation returned back to, the lidar apparatus.

Figure 7:
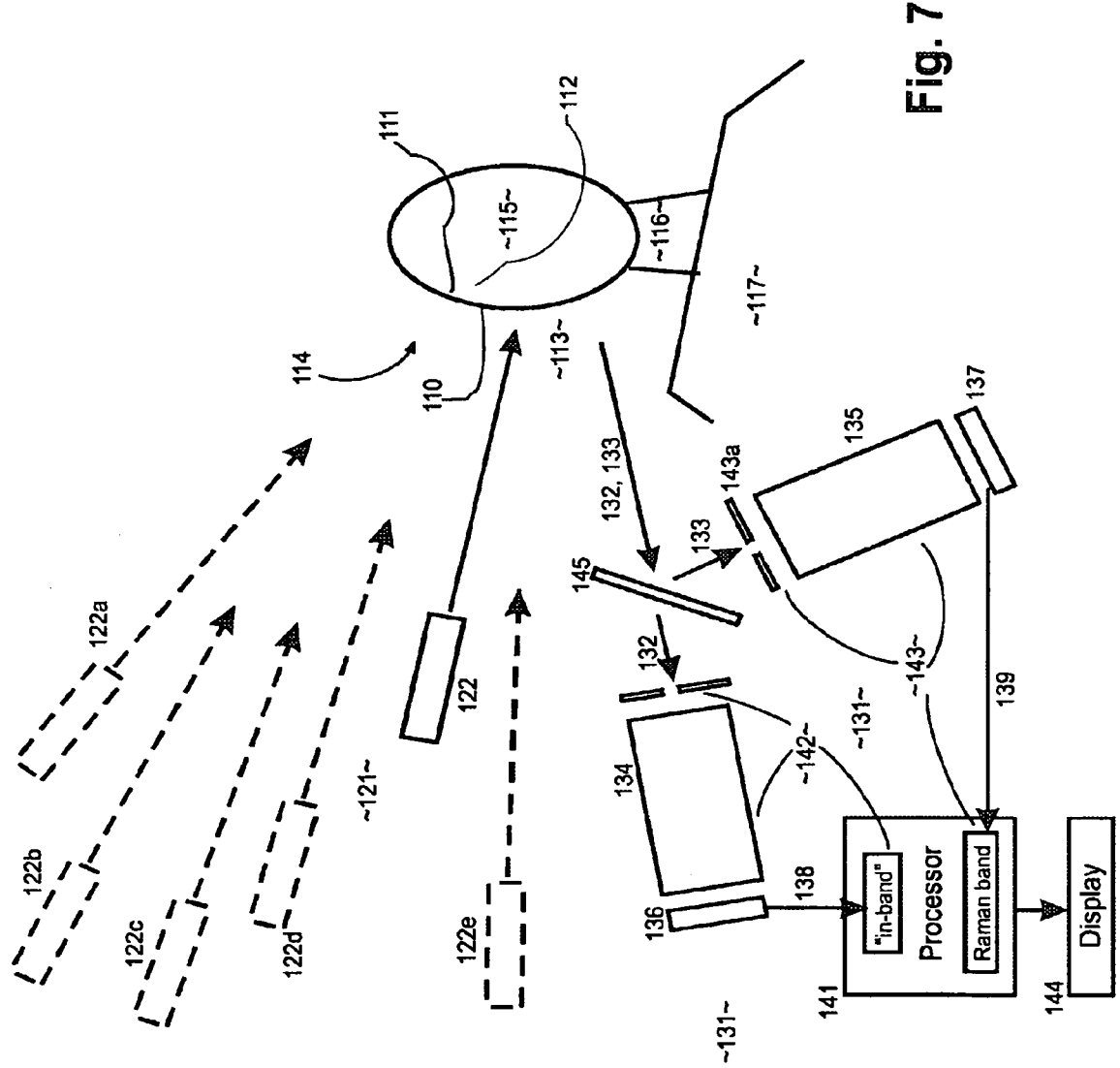
FIG. 7 is a block diagram, very schematic, of a highly preferred system, discussed in detail below, for isolating and evaluating depth zones of a subject's face and nearby bodily areas (with optional multiple added lasers shown in the broken line, and—for simplicity of the drawing—optional multiple Raman-band streak tubes represented by only a single such streak tube)
Figure 9:
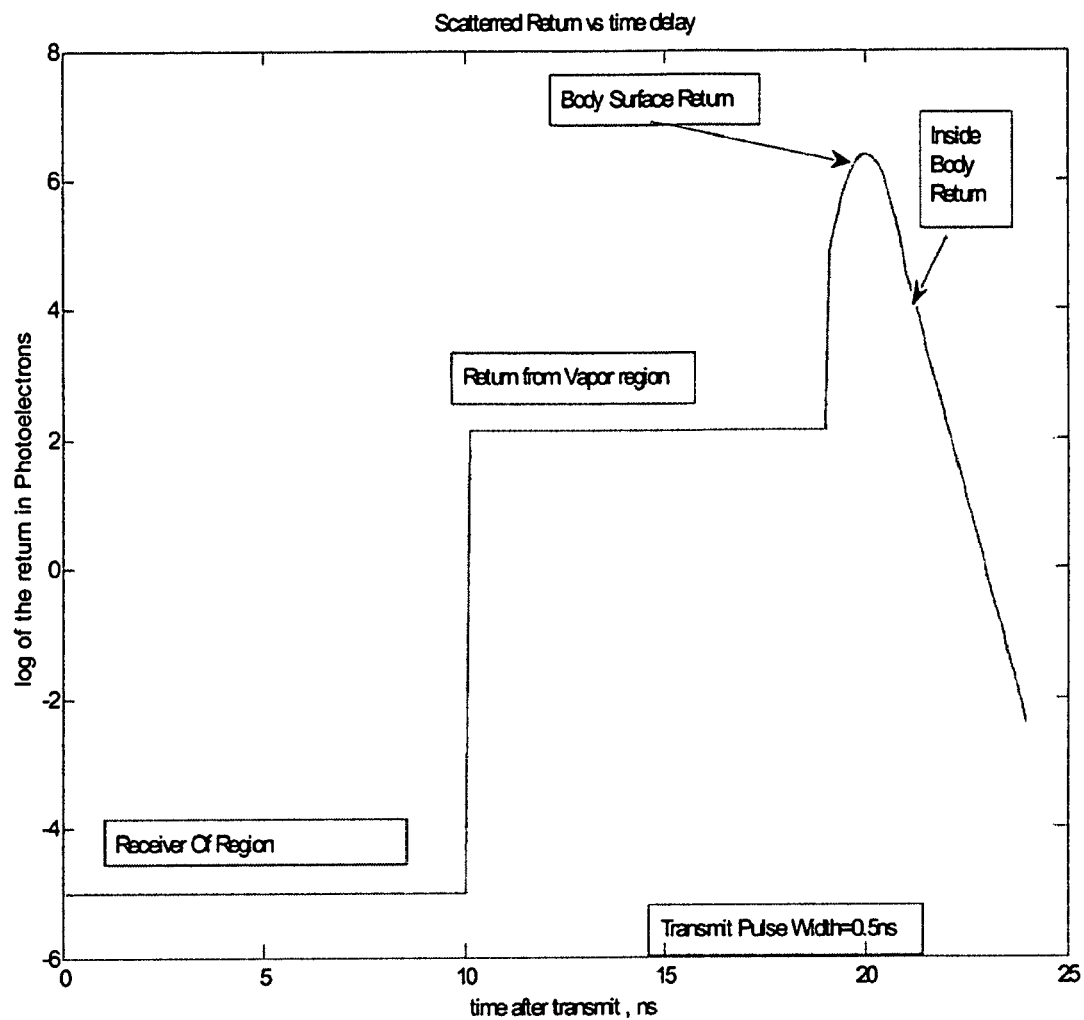
FIG. 9 is a graph of lidar return as a function of time, illustrating a basic three-zone polygraphic strategy according to preferred embodiments of the invention.
Figure 10:
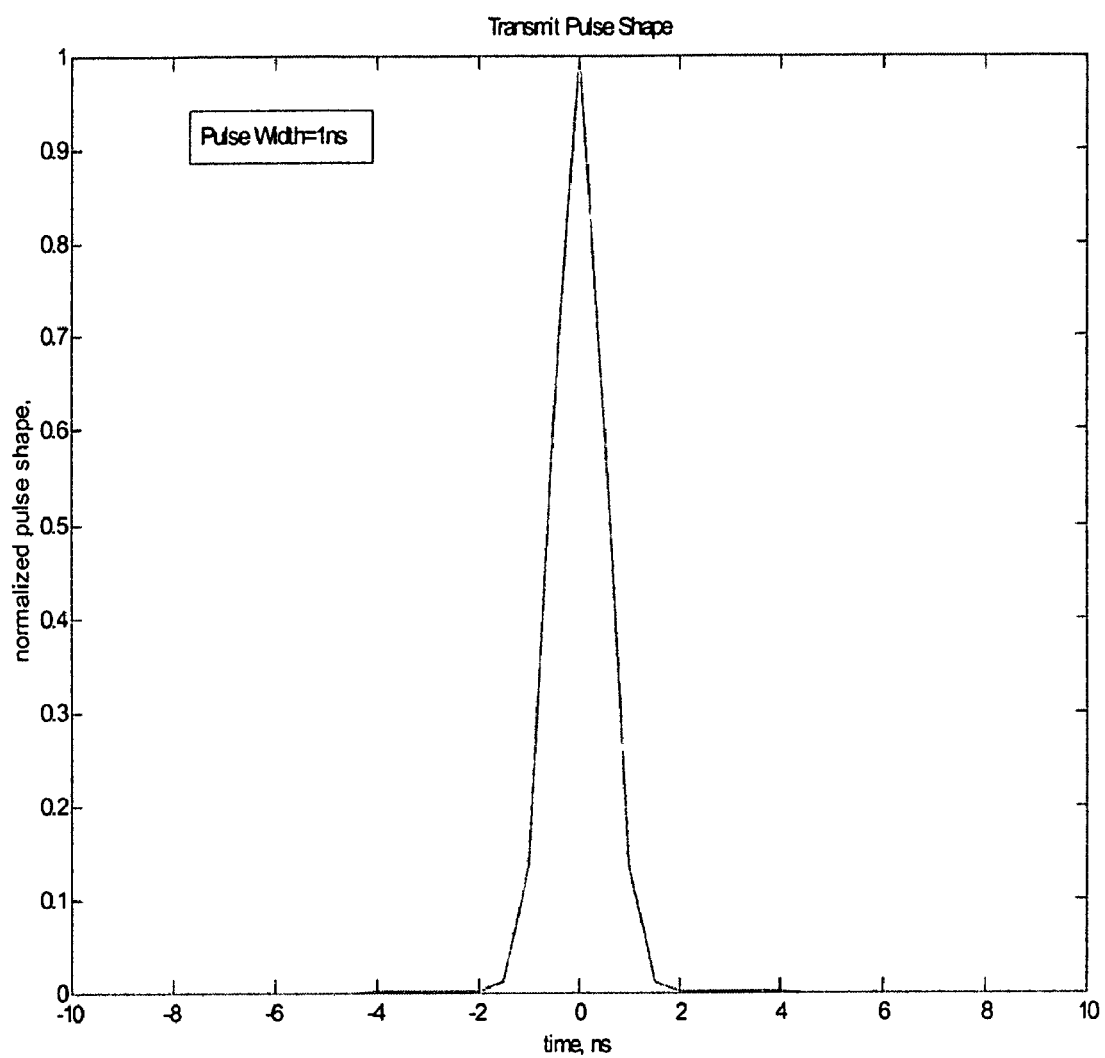
FIG. 10 is a graph of lidar pulse shape (amplitude vs. time) as used in preferred embodiments.

For purposes of the present polygraphic invention, the depth zones are:

zone 1) the subject's skin 110 (FIGS. 7 and 9) and a few millimeters of flesh 111 immediately behind the skin;

zone 2) an additional few millimeters of flesh, bone and other materials 112 within the body, behind zone 1; and zone 3) a volume of air and other gases 113 outside the body, in front of zone 1—i.e., in front of the skin and closer to the lidar apparatus.

As discussed in greater detail below, all three zones 110-113 are mainly but not exclusively at the subject's face 114 and nearby parts of the head 115, neck 116 and chest 117. Based upon this operating strategy, the apparatus (and therefore its operators) can isolate, into separate signal channels and separate analytical regimens, a number of anatomical and physiological phenomena associated with these different parts of the body, respectively. Comparisons of these phenomena, as between the different bodily regions, follow directly, as do polygraphic conclusions from those comparisons.

A very highly preferred embodiment of the present invention includes a laser subsystem, a receiving subsystem, and a processing subsystem:

The laser subsystem 121 has a very-short-pulse, single-frequency, high-pulse-repetition-frequency ("PRF") laser 122 with wavelength range of 500 to 1500 nm (ideally 800 nm), and bandwidth of approximately 0.1 nm or less. The PRF is in the range of 1 kHz to 100 kHz (ideally and nominally 10 kHz).

The pulse width is in the range of 0.01 to 1 nsec (ideally and nominally 0.1 nsec). Average power is less than 1 mW (ideally 1 mW).

The point of this apparatus is to obtain a very good representation of the three separate zones, most particularly the first few millimeters within the body where the temperature change will be determined. In addition the return-radiation amplitude from zones 1 and 2 enables determination of increased moisture and salt on the surface, indicating sweating. Still further, measurements from zone 3, just outside the body, can be used to determine increased sweating—by an increase in the return amplitude from this region.

Yet another valuable feature is a multifrequency system to determine, in all three regions, changes in chemistry. Processing of data from these regions will delineate such chemical phenomena in additional detail.

The receiver subsystem 131 is critical, to obtain:
good resolution in range (e.g. from 1 to 5 mm),
a good spot size to work with (e.g. 1 to 3 cm), and
good Raman-band resolution, in wavenumbers (denoted as "$\lambda^{-1}$"—or better as reciprocal centimeters, "$cm^{-1}$").

The return 132, 133 is best split (e.g. by a suitable frequency-selective device 145: dichroic or etalon filter, or grating) into frequency region 132 at transmitted frequency and a nearby band 133, literally shifted by about 100 to 400 nm to operate as the Raman band to sense temperature.

For each of these two bands 132, 133 ideally (as discussed further below) a respective receiver 134, 135 of streak-tube type is used to achieve very good aggregate range-resolution sampling—on the order of a millimeter. For each pulse, each band is best imaged onto a respective microchannel-plate-enhanced CCD 136, 137, to obtain photon-counting sensitivity and also to accumulate respective pulses 138, 139 on-chip before reading out the charge.

The detector 136 in the channel 142 that develops the wavelength-unshifted band (also called the "in-band channel") is not necessarily a full two-dimensional array. Rather, it may take the form of a one-dimensional array, which is sufficient to perform time resolution of the unshifted band.

Preferably this accumulation is to occur over a time period of about 1/30 second, so that motion of the body surface points 110-117 can also be accurately determined and tracked. For the Raman-scattered band 133 (approximately 1000 $cm^{-1}$) wide, around a central frequency that is literally shifted about 100 nm from the transmitted frequency as mentioned above, the scattered band is best spread over a slit 143a in front of the streak tube 135—to thereby resolve the wavenumber measurements for the scattered Raman band 133.

It is straightforward to determine the number of photons received by a nominal system, first for the receiver 136 operating at the transmission frequency, and second for that 137 operating at the Raman literally-shifted frequency—both for zone 2 (inside the body just beyond the influence of the surface). These two channels are best analyzed separately:

First, for the return in photons at the transmission frequency, analysis begins with calculation of the photon flux to the subject. That flux, for one pulse from a 1-microjoule-per-pulse laser is:

$$\text{intensity (in photons)} = \frac{\text{pulse energy (in photons)}}{\text{spot area}}$$

$$= \frac{\text{pulse energy (in joules)}/h\nu}{\text{spot area}}$$

where the pulse energy is 1 microjoule, $10^{-6}$ J, h is Planck's constant, $6.6 \cdot 10^{-34}$ m² kg/sec c the speed of light, and $v=c/\lambda$ (c divided by the wavelength); and the spot area is 1 square centimeter, or $10^{-4}$ square meter;

hence:

$$\text{intensity (photons)} = \frac{10^{-6} \text{ J}}{6.6 \cdot 10^{-34} \text{ m}^2\text{kg/sec} \cdot \frac{3 \cdot 10^8 \text{ m/sec}}{10^{-6} \text{ m}} \cdot 10^{-4} \text{ m}^2}.$$

Now, 1 J=1 Nm=1 kg (m/sec)²=1 kg m²/sec².

Thus the flux per pulse is $5 \cdot 10^{16}$ photons, into a square area 1 cm on a side.

This result is for a single pulse, and the repetition rate as noted above is nominally 10 kHz. Integrating over ⅟₃₀ second, or roughly 330 pulses, yields a 330-times-greater number of photons reaching the subject. A much smaller number of photons, depending upon a backscatter coefficient at the subject, as well as the subject/receiver geometry, propagates back into the lidar transceiver:

$$\frac{\text{received}}{\text{photons}} = \text{intensity} \cdot \frac{\text{backscatter}}{\text{coefficient}} \cdot \frac{\text{receiver}}{\text{area}} \cdot \frac{\text{receiver}}{\text{solid angle}},$$

where:

intensity is calculated as shown above backscatter coefficient is a constant at the subject surface receiver area characterizes the apparatus aperture $$\frac{\text{receiver}}{\text{solid angle}} = \frac{\text{subject irradiated area}}{(\text{distance from subject to apparatus})^2}.$$

The "backscatter coefficient", with dimensions of "per steradian"—i.e., steradian⁻¹—is a characteristic of the substance (skin, flesh, bone etc.) of interest, in the region (e.g. zone) that is involved, and for the physical mechanism that generates the backscatter. In particular different backscatter coefficients apply for the in-band radiation (having the same wavelength as the transmitted laser pulses) and the Raman signal, respectively. A typical backscatter coefficient for a human subject's skin, without sweat, is very generally on the order of 0.1 for dry skin of a subject, $10^{-4}$ for the interior of the body, and $10^{-5}$ for the air (or vapor, or other gases) in front of the skin.

Since ordinarily there are three distinct depth zones, each zone potentially having both Raman return and in-band non-Raman return, in principle there can be six distinct backscatter coefficients for polygraphy according to the present invention. The number can be higher if spaced-apart different regions of the body are involved—e.g., if one or both of a subject's hands, as well as the head, are imaged and analyzed.

The receiver area, as noted above, is the area of the aperture provided at the lidar receiver, not of the subject region being probed. To collect as much backscattered light as feasible, the receiver aperture is advantageously chosen to be large—within the constraints of practicality and cost. A suitable aperture can be a COTS component (commercial off-the-shelf), for instance three inches (0.08 m) in diameter and with area of 7 square inches (0.005 m²).

The "receiver solid angle" adjusts for the geometrical relationship between the subject region being probed and the instrument aperture used to collect optical data. For a subject surface area of 1 cm², 3 m from the lidar transceiver, the solid angle is $0.01^2/3^2 = 10^{-5}$ steradian.

Taking account of all these values, the number of photons received back from the previously discussed outgoing photon stream is for dry skin roughly $5 \cdot 10^{16} 0.005 \cdot 10^{-5}$ or $5 \cdot 10^{-9}$ times the previously calculated photon intensity of about $5 \cdot 10^{16}/\text{m}^2$. This works out to, generally, on the order of 2½·10⁸ photons/m² for dry skin, 2½·10⁵ inside the body and 2½·10⁴ in the air etc. outside the body.

It remains to describe electronic signals that arise, responsive to this return photon flux striking the streak-tube cathode or other photoelectric conversion device—as photoelectrons ejected from that cathode or other device:

$$\frac{\text{received}}{\text{photoelectrons}} = \frac{\text{received}}{\text{photons}} \cdot \frac{\text{quantum}}{\text{efficiency}},$$

where:

received photons are calculated as shown above, and quantum efficiency is a constant of the cathode in the streak tube.

Modernly the conversion efficiency (or "quantum efficiency" as above) is greatly improved over that of only one to three decades ago. Values of 50% are now common—in other words, on the average roughly one electron can result from each two photons received. Photoelectron flux is accordingly just over $10^8/\text{m}^2$ for skin, $10^5/\text{m}^2$ for the interior, and $10^4/\text{m}^2$ for the air etc. in front of the skin.

The noise level in estimating the surface location (i.e. range), assuming a well-known pulse shape, is the transmitted pulse width divided by the square root of the signal-to-noise level. In this case for PRF of 10 kHz the signal-to-noise ratio equals the total number of photoelectrons or $330 \cdot 10^8$. Taking the square root here yields nearly $20 \cdot 10^4$.

This value allows the system to resolve the surface position every ⅟₃₀ second—assuming a pulse width (duration) of 1 nsec—to better than 1 mm in the depth or "range" direction. This is accomplished by a sophisticated departure from the usual operation of a lidar sweep tube, as explained now:

In a very simple lidar operation, the pulse width of 1 nsec can translate directly into range resolution by virtue of the basic relationship between lidar pulse width and the round-trip travel time just in front of the subject's skin. The correspondence is set by the speed of light: $c \cdot \Delta t = 2d$, where $\Delta t$ is the round-trip travel time and d is the one-way uncertainty in skin location.

As developed in this way, the range uncertainty (best resolution) is found as $d = c \cdot \Delta t/2 = 1.5 \cdot 10^8$ m/sec·$\Delta t$. With $\Delta t = 1$ nsec, the range resolution is $d = 3 \cdot 10^8 \cdot 10^{-9}/2$ m=15 cm. Such coarse resolution would be of limited utility for polygraphic purposes.

The present invention, however, contemplates achieving far finer resolution by either of two separate approaches, or combinations of them:

operating the streak tube at extremely fast sweep speeds; or using a pulse width much finer than 1 nsec.

Pulse width of 1 nsec has been attainable for about the last decade, and so was readily available when the parent application or precursor of this document was first filed in the patent office. In addition, very fast streak-tube sweep has been possible for many years. Hence the fast-sweep approach to fine range resolution for polygraphy was usable and entirely effective when that parent case was filed.

The two techniques will now be taken up in turn:

(1) Picosecond sweep enables range resolution finer than 1 mm. Even though the pulse width corresponds to 150 times that distance, as demonstrated in the preceding paragraphs, the extremely fast sweep—optionally combined with very responsive gating—can display the critical distance, immediately in front of the skin, over a sizable fraction (e.g. a few percent to one hundred percent) of the height of the streak-tube anode (and screen). This enables a person or apparatus to "see" 1 mm as a relatively small distance increment on the anode.

In effect this technique depends upon careful interdesign as between operations at the lidar transmitter and receiver, respectively. Given these guiding principles, a person skilled in the field of lidar design can proceed straightforwardly to apply fast-sweep technique, with transmitter/receiver characteristics exploited for gating strategies, to attain range resolution better than 1 mm.

(2) Subnanosecond pulse width is now achievable. Although fine resolution has long been obtainable through fast streak-tube sweep as just described, there is now an even simpler, easier and preferable way to accomplish the desired resolution goal. This strategy takes advantage of the most-modern lasers and laser-control apparatus, capable of transmitting pulses as short as a tenth of a nanosecond or even a hundredth of a nanosecond.

For example with $\Delta t=0.01$ nsec (10 psec) the range resolution is $d=3\cdot 10^8 \cdot 10^{-11}/2$ m=1½ mm. With 1½-mm range gating in transmission, and matching that in the receiver, the system thus provides natural range resolution of 1½ mm. The shorter transmitted pulses make this possible, now in 2008, without resort to relatively extreme measures such as an ultrafast streak-tube sweep.

As will now be appreciated, incorporating such extremely fast sweep too—in combination with the shorter pulse and gate—enables resolution better than 1 mm, in the depth or range direction. In this case the resolved volume inside the body is 1 mm×1 cm×1 cm, which is impressive in itself.

In addition the system can resolve several gates or subzones inside the body, and can see the vapor region just outside the body—and observe changes in all these regions due to sweating. The result is a unique capability of determining deception, never before available. Analyzing all three regions in conjunction yields much more information than in conventional polygraphy. Being unaware that these more-complex data are being acquired, and further unaware of the analytical refinement available by crosscomparisons of such data, subjects cannot "beat the system" as easily.

Turning briefly now to the Raman band, the same equations apply except that the backscatter cross-section and therefore the return photoelectron current are about five orders of magnitude smaller. Consequently, most-typically the Raman return can be used to estimate temperature (or other physiological parameters) only with less-fine resolution—spatial, temporal or thermal.

Figure 8:
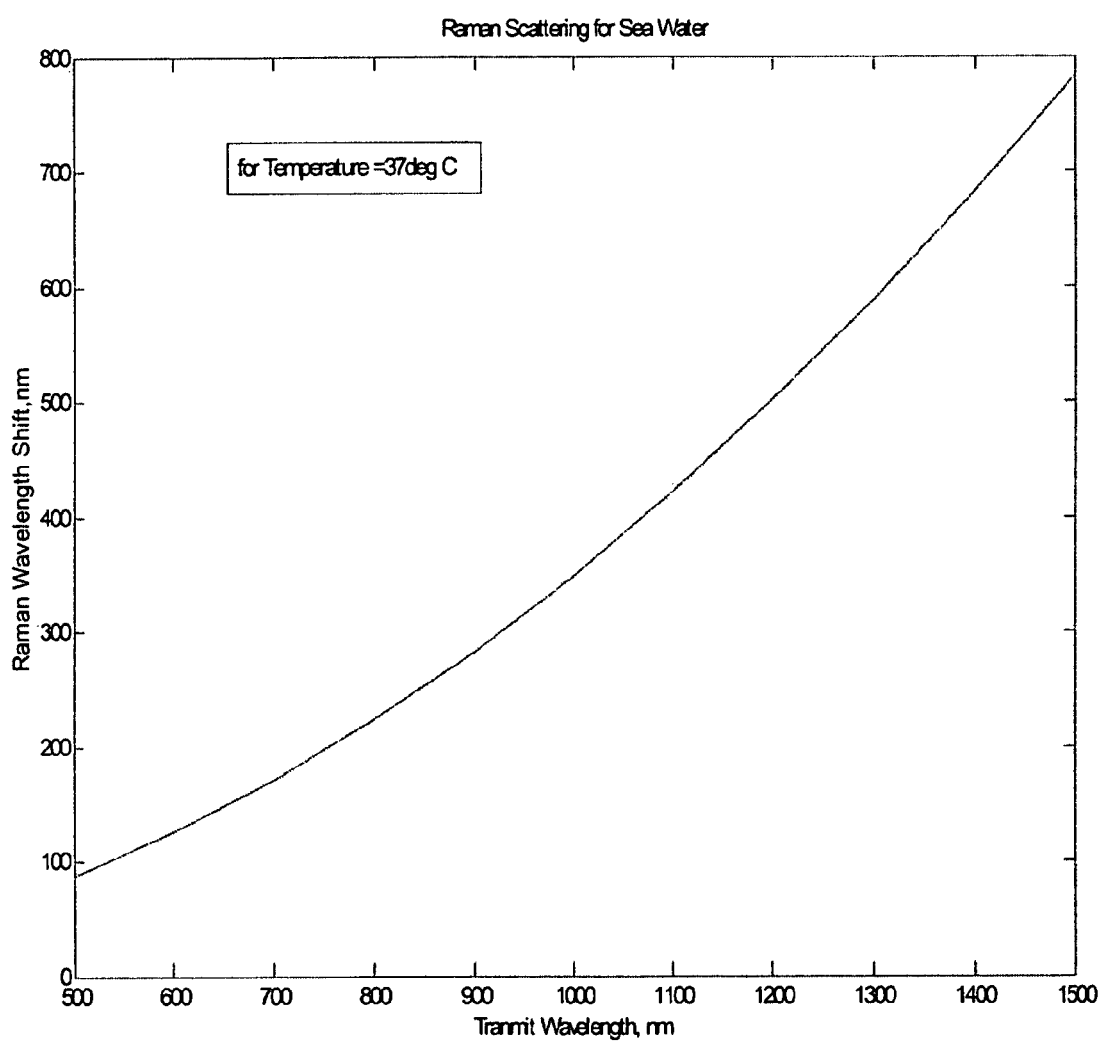
FIG. 8 is a graph (after Lee et al., "LIDAR Measurement of Water Temperature by Using Frequency-Shifted Raman Scattering", 38 *J. Korean Physical Soc. No. 6*, 659-65 [2001]) of Raman wavelength shift per se as a function of transmission wavelength.

In general, to measure temperature the apparatus receives approximately 1 photoelectron from one cubic centimeter of volume within the body. A preferred approach, similar to Lee's, is to estimate the measured mean wavenumber shift (literal shift) of the Raman wavenumber band with temperature—which Lee found to be approximately 1 cm$^{-1}$ per Centigrade degree, for seawater (FIG. 8), at a laser-transmission wavelength of 532 nm.

To estimate a $\frac{1}{20}$ degree Centigrade change every 10 seconds, i.e. with 10-second integration, the error in estimating the Raman wavenumber band shift per se should be kept under 0.05 μm$^{-1}$. To estimate that frequency shift (or equivalently wavenumber shift), the "pe" (photoelectron) data for each wavenumber bin in the Raman band, at the streak tube, is preferably fitted to a Gaussian curve as suggested by Lee. This is done for a range corresponding to a position within the subject's body. Next the algorithm should form the quantity:

$$MeanWavenumberEstimate = \frac{\Sigma(\lambda^{-1})pe_i}{\Sigma pe_i}.$$

This expression yields the literal shift from the transmission frequency, which is then used to estimate the temperature in the body. Error in this quantity can be determined from:

$$\Delta MeanWavenumberEstimate = MeanWavenumberEstimate \cdot \frac{\Sigma\sqrt{pe_i}}{\Sigma pe_i}.$$

For the examples above, and with the expected Gaussian shape for the Raman band as shown for Lee's data, then when integration can last for ten seconds (amounting to 100,000 pulses), this expression estimates relative mean wavenumber with an error of roughly 10$^{-4}$. Such measurement depends on having a relatively stable or quiescent subject. Based on Lee's result, this implies temperature error of 0.3 C for 10-second measurement.

People skilled in this field will appreciate that the adverse influences of low Raman scattering, on temperature resolution in time and space, can be mitigated in various ways—i.e. not only by relatively long integration times or by increased measurement volume in the body, or both. For example in quite extraordinary circumstances it can be permissible to apply greater transmitted pulse power—which may undesirably heat a local region of the subject. This effect should be carefully monitored to avoid injury, and usually to avoid alerting the subject to operation of the apparatus.

Another mitigation method, particularly when wholly covert operation is not required, may involve a temperature relay material. This could call for embedding in, or affixing to, the subject's skin a small piece of material that tracks the subject's local temperature and provides much higher Raman response.

The most effective apparatus and method for overcoming low Raman scattering involve multiple lasers. Their contributions to e.g. temperature-measurement quality can be made additive, even if the lasers operate at slightly different wavelengths or are directed to slightly different points on the subject's body—or both.

Such a strategy is taken up in detail below. It is extremely important for best results, especially as to temperature-scale resolution and the temporal and spatial resolution of temperature measurement.

A skilled person can configure some preferred embodiments of our invention to use much lower pulse energy, which—due to the techniques now available (and available in 2002) in the measurement community—enables improvement in measuring the returned spectral-response accuracy to the quantum limits imposed by the Uncertainty Principle.

(Such enhancement is already embodied in the two equations relating to "MeanWavenumberEstimate", presented some half-dozen paragraphs above.) This in turn enables measuring the centroid shift with an accuracy determined by the number of received photons over the Raman band of interest shown by Lee. This fact is well known to people skilled in these sorts of measurements.

The scattered signal is reduced due to the smaller volume, in the environment of the present invention; however, implementation of Lee's approach (see below) still yields a very large number of photons to work with. This is true even if laser energy per pulse is reduced to eye-safe levels (e.g. at our range of interest, say 5 m) of 2 mJ per pulse (100 times less than used in the Lee paper.

In another mitigation strategy, briefly mentioned just above, the present invention can employ up to hundreds of different lasers e.g. 122a through 122e (FIG. 7) or laser diodes or the like, operating at or in very slightly different frequency bands and striking slightly different areas on the subject's face and neck. This strategy exploits an important characteristic of Raman spectrometry namely, that the excitation need not be at precisely a particular frequency or wavelength (as it must in fluorescence), but rather can be provided at frequencies over a range. By constraining the system so that the different lasers impinge on different areas, the instrument design can ensure that only one can possibly hit the eye of the subject; therefore the system is eye-safe.

Of possibly even greater importance, this technique also can be used to mitigate the limitations due to relatively low Raman scattering, discussed elsewhere in this document. In this regard specifically, preferred forms of the receiving means of the invention comprise means for receiving pulses due to the plural laser emitters, respectively. People skilled in this field will appreciate that, correspondingly, one or more data-processing modules 141 of the apparatus should derive respective information from pulses received due to the plural laser emitters.

The processor(s) 141 also should be programmed to combine information derived from received pulses due to the plural laser emitters, respectively—to generate enhanced information. People skilled in this field further will be aware of methodologies for so combining the various pulse data streams, to cumulatively refine signal-to-noise beyond what any of the individual data streams can achieve.

In this way the temperature test volume within the subject's body can be reduced to much less than the cubic centimeter mentioned earlier. With aggregation of a sufficient number of lasers, Raman technique for temperature measurement can be associated with volume of e.g. 1 cm×1 cm×1 mm (depth) as specified above for the simpler in-band measurements.

This refinement of temperature depth resolution by at least one order of magnitude (from the previously suggested 1 cm), if achieved in the most-straightforward manner, calls for ten or more lasers 122a-122e (FIG. 7), and such a change may be moderately costly. Except where price is a secondary consideration (e.g. perhaps for highest-stakes government interrogations), however, a greater concern is the requirement for, ideally, a separate Raman-band channel 143 for each laser. In such a system the most expensive component is a separate streak tube 135 for each laser—e.g., ten or more streak tubes.

Many possible tradeoffs are available to moderate this cost: the spatial resolution for temperature may be relaxed to e.g. 5 mm (from 1 mm as for other, nontemperature, measurements), or the Raman-band PRF and sampling rate to 15 seconds (from 10), or the thermal resolution to $1/10$ or $1/15$ degree (from $1/20$); or very greatly enlarging the aperture to e.g. five or even ten inches. Other options include time-sharing one or more of the streak-tubes, as well as substitution of very fast electronics for time-resolving the Raman signal.

People skilled in this field will appreciate that refined spatial resolution, for temperature, exceeding an order of magnitude can be achieved by combinations of two or more of such tradeoffs—taking, for example, a factor in the range of e.g. 1.1 to 2 from each of several techniques for an overall multiple of 10 to 100.

In other contexts (i.e. not for temperature), such multilaser technique increases accuracy of centroid measurement by a factor of three to ten.

In addition, using a larger aperture at the receiver can increase centroid accuracy by another factor of three. Also, given the setting for use of the present invention, an interrogator can ask slightly different questions in multiple time periods. Upon combining the results from such intervals, such tactics can still further improve the accuracy of centroid measurements.

The Processing Subsystem 141 operates on the two segregated return bands, in two respective processing channels 142, 143. The in-band channel 142 first determines the range to the subject's surface (e.g. skin) 110 from the return waveform, and very accurately locates that surface—and thereby delineates the three zones dynamically, e.g. every $1/30$ second as suggested above.

By thereafter tracking this surface, the apparatus obtains the heart rate, breathing rate and gross motion of the subject. From such information, and particularly from changes in such local motions, the polygraph or its attending polygrapher can determine whether the subject is under increased stress.

It is remarkable that such detailed and useful data can be derived from the in-band channel 142 alone. As will be detailed shortly, however, the Raman-scattered band—as analyzed in the offset channel 143—provides even more-informative data.

Amplitude at the surface 110 can also reveal changes in moisture content (sweat) which usually decreases the return at the surface by increasing the smoothness of the surface. This effect runs counter to the commonly observed "shininess" of perspiration on the skin, in other environments.

Processing for this surface 110 advantageously employs an empirically determined so-called "match filter shape" selected for each setup. More specifically, each pulse from the laser follows a time-shape that is particularly chosen to yield a corresponding extremely distinctive pulse shape in the return. (The transmitted pulses can all be identical, or for even greater selectivity each can be unique.)

Each return pulse is then automatically compared in shape with the corresponding outgoing pulse, on a weighted-time-increment basis. The matching time increments within each returned pulse are summed to develop a return-amplitude value for that pulse, and the resulting sums for different pulses can then be used to represent the effective overall return amplitudes just as if they were simple pulse heights.

Turning now to the Raman-scattered band, as analyzed in the offset channel 143: to understand the processing of the Raman-scattered band, next consider zone 2. This, again, is a zone that is just below the surface 110, e.g. roughly 3 mm inside the body, but does not contain the surface return.

This zone is normally dominated by properties of its blood content. In its Raman-scattering behavior the latter is characteristically similar to salt water, to first order, and therefore has a return similar to that indicated in a technical paper by Lee et al., which will be taken up in greater detail below.

The Lee algorithm utilizes frequency change, literally, to determine temperature. Analogous temperature determination is set forth in the parent patent application of this document: with a similar algorithm, the apparatus of the present invention uses the measured results from the CCD for each scattered wavenumber away from the transmitted frequency (at the selected range element inside the body)—and applies those results to determine, once again, the literal frequency shift per se of the Raman band at the selected range zone inside the body.

It will be understood that most well-known uses of polygraphy are for analysis of humans. In principle, however, the present invention is not so limited. For example many applications in experimental psychology of nonhuman creatures are within the scope of the invention and can be potent tools for noninvasively exploring, exploiting and even expanding the intelligence of such creatures.

Heretofore, since few animals appear to be capable of rational speech, such experimental work has been hampered by need to observe animal subjects very closely and continuously, and to devise indirect means of probing animal perceptions or reactions. As applied to animal research, the present invention—in straightforward variants suited to nonhuman creatures—thus very greatly broadens the range of instrumentalities available for divining and analyzing what is going through the minds of such creatures (and this without sacrificing or harming the creatures).

Thus in its most-highly-preferred forms the invention uses an active camera system, very finely range-gated with a very short-pulse laser. The range-gate return is applied to locate the surface of the subject's skin in relation to the apparatus.

People skilled in this field will appreciate that for most or all polygraphic purposes it is sufficient to locate and track the surface in a relative sense, i.e. to analyze small changes in position—and phenomena in the zones 2 and 3 relative to the skin surface—rather than determining the absolute distance between the skin and the apparatus. (As a practical matter, the latter procedure is often readily feasible, but simply may not be necessary.)

In any event it is generally important to relocate the skin surface rather frequently, as detailed elsewhere in this document, to avoid losing operative locations of zones 2 and 3. Further, motion in itself sometimes implies increased stress, particularly motion at certain spatial frequencies—for instance those corresponding to trembling that can be imperceptible in simple visual observation.

For this purpose it is desirable to range-gate to millimeters. As detailed earlier, this objective calls for pulse operation in the range of a few picoseconds to one nanosecond.

With skin position established, remaining variations of the signal provide the other parameters mentioned above. For instance the relative degree of scattering at the surface, and particularly its variation over time, serves as an instantaneous indicator of moisture (i.e. sweat); and if desired some limited amount of biochemistry in that moisture can be determined through analysis of spectral lines in the return.

Monitoring of minute periodic skin-range fluctuations, generally at frequencies of very approximately one per second (but between roughly 0.3 and 2.5 Hz)—and found at, for instance, the subject's temples—yield the heart rate. Like movements at the upper chest, throat, or nostrils but slower (e.g. at frequencies in the range of 0.01 to 0.3 Hz) signify the respiratory rate; and at the eyes, the rate of blinking.

Small cyclical positional fluctuations in other areas, or even in the same areas (but characterized by substantially higher frequencies, e.g. 5 to 50 Hz), can reveal even a very slight trembling. In some of these operations it is necessary to carefully discriminate beats (in the interfering-frequency sense) of the physiological activity against the pulse frequency of the laser.

Hence a preferred embodiment of the apparatus filters the positional information into various frequency ranges, and separately monitors the amplitude and exact frequency of the data in each range. These signal channels can be read out on a display at the time of data acquisition—e.g., during an interrogation, which enables the equipment operator to dynamically control the course of questioning, as is the state of the art in conventional polygraphy—or can be saved for later, or preferably both.

Automatically derived correlations among the several parameters, and their time derivatives—i.e., acceleration, deceleration or degree of abruptness in these changes—can also be characterized (e.g. "concern", "anxiety", "panic") and displayed or recorded. These if preferred can be treated as only advisory to the operator, whose professional interpretation is generally accorded greater reliability.

Preferred embodiments of the present invention, however, are capable of a reasonable degree of objectivity in output readings and their interpretation—much more so than in conventional polygraphy, as will be understood from the overall presentation in this document. This is partly due to the superior ability of the invention to deal with the problems of false positives and negatives.

While most of the equipment operates in an active mode (i.e. by analysis of radiation reflected by the subject from a pulsed laser), operation in the infrared enables collection of passive data as well—particularly including the subject's body temperature, found from its own very slight thermal radiation. An alternative or confirming measurement of temperature, however, can be found from very slight frequency changes in the laser return beam (following the general paradigm taught by Lee et al.).

Relative to many established uses of lidar (particularly monitoring of small objects within turbid media), the present application intrinsically enjoys an unusually favorable signal-to-noise ratio. Preferred embodiments therefore can extract accurate and useful bioparameters from a relatively loosely operating system.

If desired this apparatus can be placed in a housing that has the general appearance of an ordinary video camera, or for that matter a potted plant or anything else. The same housing, in fact, can also accommodate a conventional video camera—or, as preferred, the lidar device itself can be configured and operated to acquire substantially conventional-appearing video images as well as all the data discussed above.

To minimize subject awareness, the device can be operated in the infrared, with careful attention to eye-safety and sensitivity precautions. What is desired is ideally an eye-safe wavelength of 1.5 µm. The invention also should be practiced with careful attention to invasion-of-privacy issues, generally as noted earlier.

Several variants illustrated and discussed in this document emphasize the very great variety of alternative forms of both apparatus and method. In particular, in one suitable geometry a low-power, short-pulse, eye-safe IR lidar transmitter 12 (FIG. 1[A]) transmits a pulsed beam 18 directed toward the subject 10 several times per second. A scattered pulse beam or reflected pulse beam is returned by the subject and received by a lidar receiver 14.

Figure 1:
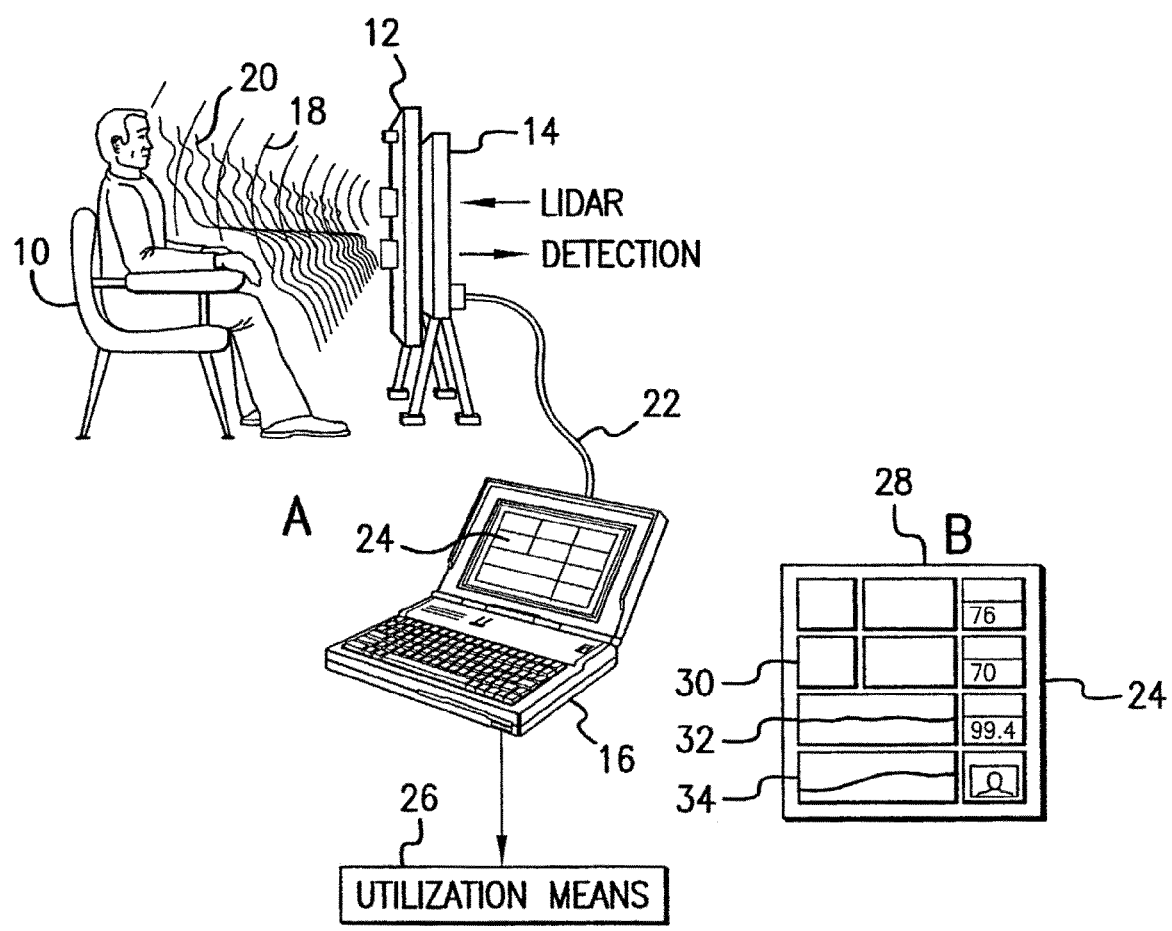
FIG. 1 is a two-part conceptual illustration of a preferred embodiment of the invention, the (A) portion being a block diagram, showing lidar pulse interaction with a subject, and a computer controlling the lidar transmitter and monitoring pulse returns to the lidar receiver to develop a display for consideration by a human operator—and other forms of utilization means as well, the (B) portion being a conceptual view of data display at the computer.

The latter is, but need not be, generally collocated with respect to the transmitter 12, so that the two considered together form a transceiver. The receiver 14 is connected to a computer 16 by a wire, cable or similar device 22, or by a wireless connection. Associated with the computer is a display 24 (FIG. 1[B]).

The computer 16 and display 24 are provided with the requisite hardware and software to interpret the data received by the receiver 14, to produce various desired visual outputs (FIG. 1[B]) for interpretation by a human operator—as well as being transmitted to other utilization devices. Hence the display 24 exhibits various indicia based upon correspondingly various physiological parameters. These parameters most-typically include, but are not limited to, a subject's heartbeat 28, respiration rate 30, and body temperature 32.

Also preferably exhibited is an output 34 created by automatic analysis of one or more of the aforementioned physiological parameters, or other physical parameters. This output 34 is produced by appropriate software included in the computer 16 and used to demonstrate or indicate visually whether the subject is under stress, as is most-typically the case when a subject is not telling the truth.

The computer 24 is also connected (not shown) to, and controls, the lidar transmitter 12—enabling radiation pulses from the latter to be directed toward various locations on the head and upper torso of the subject, and also enabling modifications in frequency of the pulse based upon the type of parameter of interest. Such control can be performed manually; or the transmitter 12 can be allowed to automatically scan the body of the subject as well as automatically modify the frequency.

The various parameters are analyzed based upon detecting and responding to change in distance between the transceiver and the subject's body, as would be created from movement of the skin due to a subject's heart rate and respiration rate. Also, shift in frequency of the received pulse, relative to the transmitted pulse—as well as relative degree of scattering at the skin—are also used to measure the various aforementioned parameters, as well as moisture on the skin.

A laptop or other computer 16 displays these measurements in near-real-time to aid an interrogator in determining stress in the subject, and thereby in assessing truthfulness. The various apparatus controls, including scanning of the subject's features, can be either completely automatic or completely manual, or combinations of the two.

The display is advantageously made to present all the key data both graphically and numerically (FIG. 1[B]), and with a multiparameter-integrated figure of merit 34 as noted above. In some applications, most particularly outside a direct-interrogation context any of these (but particularly the last-mentioned) may be used to operate other devices 26, sometimes called "utilization means".

Such utilization means may incorporate any of a very great variety of devices. These may include, but are not limited to, access controls for doors, vehicles, computers, financial information or money (e.g. ATM machines) and so on. Displays and other information can be interpreted by a human operator, as well as or instead of being transmitted to utilization devices.

Figure 2:
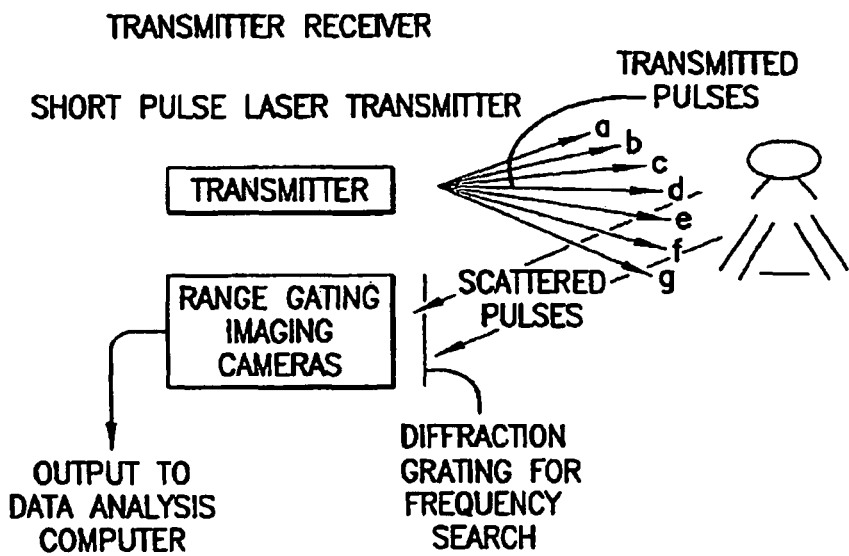
FIG. 2 is a transceiver diagram (subject to variant interpretations as explained below) representing more specifically the temporal/geometrical form of the pulses—and showing spectral and temporal resolution of the return in the front end of a detector (FIG. 2 shall be understood to illustrate application of any one of several forms of lidar system in preferred embodiments of the present invention—including scanning, mapper, and bistatic lidar versions, and also certain alternatives discussed below)

FIG. 2 shall be understood to illustrate application of any one of several forms of lidar system in preferred embodiments of the present invention. These include the three previously discussed streak-tube lidar versions, and also certain alternatives that will be discussed below. The three streak-tube-based systems will be introduced first:

Scanning system—First, as understood to illustrate a scanning system, FIG. 2 shows how it is possible to illuminate very shallow segments of the image successively—by a series of pulses a-g of the laser, directed in progressively shifted directions to scan over relevant parts of the subject's body—particularly where skin is exposed. This shifting of direction is preferably provided by a scanning mirror or set of mirrors, suitable angular rotation being obtainable by any of a great variety of means (such as a spinning polygonal mirror); or by a translating device closely analogous to the translating systems disclosed in the art.

In such a system, each pulse generates a two-dimensional image as previously mentioned—that image plane passing through the transceiver position and being extended in one direction a-g of pulse propagation. As to the nearest image facet of the subject volume, each pulse generates essentially a single pixel row.

The successive pulses in the aggregate produce a three-dimensional image in which no remapping is needed—the interpretation of the image is far more natural, as seen in the cited work of Bowker et al.—and the physical apparatus is somewhat simplified by absence of the fiber-optic remapper. To achieve adequately fast overall-frame rates (at least 10 Hz and preferably 200 Hz, as noted earlier)—for visualizing a subject's shivering, or blinking, or other relatively rapid bodily activity—the entire scanning operation must complete its cycle in a small fraction ($\frac{1}{200}$ to $\frac{1}{10}$) of a second.

This leads to a high laser-pulse-rate requirement, for instance on the order of very roughly 10 kHz—which would enable a 160 Hz frame rate for a low-resolution 64-pixel-row frame. Such rates are possible but somewhat drive up the cost of the apparatus; and a 64×64 frame is relatively unsatisfactory in terms of studying the subject's features and behavior visually.

At current-day technology, however, a medium-high-resolution system is not readily attainable in a pure scanning system. Laser pulse rates of about 80 kHz would be required for 100 Hz frame rate and a medium-high-resolution 800-pixel-row frame; as will be seen, these frame and resolution objectives can be achieved, but using a preferred embodiment that is a variant system described below.

In a pure scanning system the transmitter and receiver are most preferably collocated. For purposes of such a system FIG. 2 shows them separated only for convenience or practicality of illustration.

Remapper system—Second, as understood to illustrate a remapper system, FIG. 2 shows how each laser pulse incorporates an array of pixel rows a-g. Here, unlike the interpretation just presented, the entire subject is illuminated in each laser pulse.

The entire returning two-dimensional subject image is then remapped into a single line, and that line preferably scanned in a streak tube to develop a three-dimensional image—which as mentioned earlier, is scrambled. The remapping is readily unfolded, however, by simple computer operations.

A major advantage of this type of system is that the overall frame rate is the same as the laser pulse rate, rather than being slower by two to nearly three orders of magnitude. In a pure remapper system, as in the scanning system, the transmitter and receiver are collocated. FIG. 2 is to be understood as illustrating such collocation.

This arrangement does have drawbacks. Image resolution is limited by the preestablished number of pixels in the fiber-optic remapper, and arrays exceeding 64×64 pixels are progressively more costly or awkward—and the energy in the laser light is divided among the entire complement of pixels. Thus although high frame rates are feasible, a medium-resolution image is not readily available in a pure-remapping system.

Bistatic system—Third, as understood to illustrate a bistatic system, FIG. 2 shows how the transmitter and receiver are not collocated but rather separated by some sizable angle. As mentioned earlier, this kind of geometry produces a relatively more complicated image; but once again the image can be reconstructed by a computer. A bistatic system can be operated either with a scanning transmitter and scanning receiver or with a remapper, or in some cases both, as preferred.

Hybrids of the scanning and remapping systems are also possible and within the scope of the invention. As will now be understood, these different systems simply represent different ways of dividing up space and time for convenient and effective imaging.

Thus for example a remapper can be provided, but rather than remapping an entire image the device can be formed to remap only some segment of intermediate shallowness. The laser pulse is angularly stepped or scanned, as in the case of the pure scanning system, but not as many steps are required.

Here computer reconstruction is required, but a smaller amount of data is handled per laser pulse. The number of pulses per full image frame, and the number of pixel rows in the remapper, are traded off against one another to optimize the overall system.

This hybrid system enables provision of an intermediate-resolution image at high pulse rates. For example, 800 pixel rows in 200 Hz frames would require 160 kHz laser pulses in a pure scanning system—and would be mechanically impractical in a pure remapping system.

Such a frame-rate/resolution specification, however, is implemented straightforwardly with a hybrid. In one preferred embodiment the remapper has 1100 pixel columns and 2 pixel rows (remapped to a single line of 2200 pixels total, which is just over half the pixel complement of a more-traditional 64×64 remapper), with the laser pulsing at only 200 to 400 Hz and the scan system stepping the beam by two pixels between pulses. This system has a very creditable near-photographic 1100×800-pixel image, and a frame rate in the range of 100 to 200 Hz.

As already mentioned, streak tubes are not the only suitable time-resolution systems for use with lidar imaging in the practice of the present invention. Other exemplary systems use instead an array of small photomultiplier tubes (PMTs), or avalanche diodes, or a microchannel plate with a charge-coupled detector (CCD) array.

These are all amenable to independent time-gating of individual pixels, which is desirable in preferred embodiments of the invention. Also they are all effective at eye-safe wavelengths, which present-day streak tubes do not handle optimally.

In such an array, either the individual PMTs, diodes or CCD elements are tiny or an additional optical-coupling stage is used to spread the return laser beam, and essentially match it to the dimensions of the detector array. The array itself may be, merely by way of example, 64×64 elements.

The distance to the subject is ideally under about 10 m, and depending upon the several variants and the other parameters discussed above this may lead to pixel resolution on the subject of, for example, about 3 mm. Depth resolution should approach 0.3 mm. Although in principle data can be cached for later manipulation, this would preclude real-time preliminary assessment by an operator; therefore each pulse preferably is returned, sensed and analyzed before, or substantially at the same time as, the next pulse.

The scattered pulses are spectrally dispersed as by a diffraction grating, so as to enable the simple spectrometry mentioned earlier; and also range-gated. This means that the distance to impingement of each pulse on the nearest part (for that pulse) of the subject's body surface is used to start the time-resolution processes of the receiver. More-complicated gating is possible—as for example setting the gate for each pixel by the previous image for that pixel, respectively.

One way in which such processes can provide extremely fine time resolution is by a streak-tube sweep such as discussed in the documents mentioned earlier. Those documents explain how the time interval of return of each pulse is essentially mapped to position along one dimension (e.g. height) of a streak-tube screen, as illustrated in the drawings of the patent documents and therein-cited art incorporated by reference.

Such mapping causes that dimension on the screen to represent distance from the lidar transceiver, or in other words depth into the subject's body, as shown and explained at length in those earlier documents. As also mentioned in certain of the cited art, time resolution can be obtained through use of extremely fast electronics, without resort to a streak tube.

Meanwhile a transverse direction (perpendicular to the scan-sequence direction) is preserved as a spatial image direction, so that in the scanning-lidar form of the invention the streak-tube screen represents a tomographic visual section partway through the patient's body. As a patient's skin and flesh are not opaque but rather turbid media, the analyses made by the automatic equipment extend slightly into the patient's body—to depths that are readily determined by simple systematic measurement.

Figure 3:
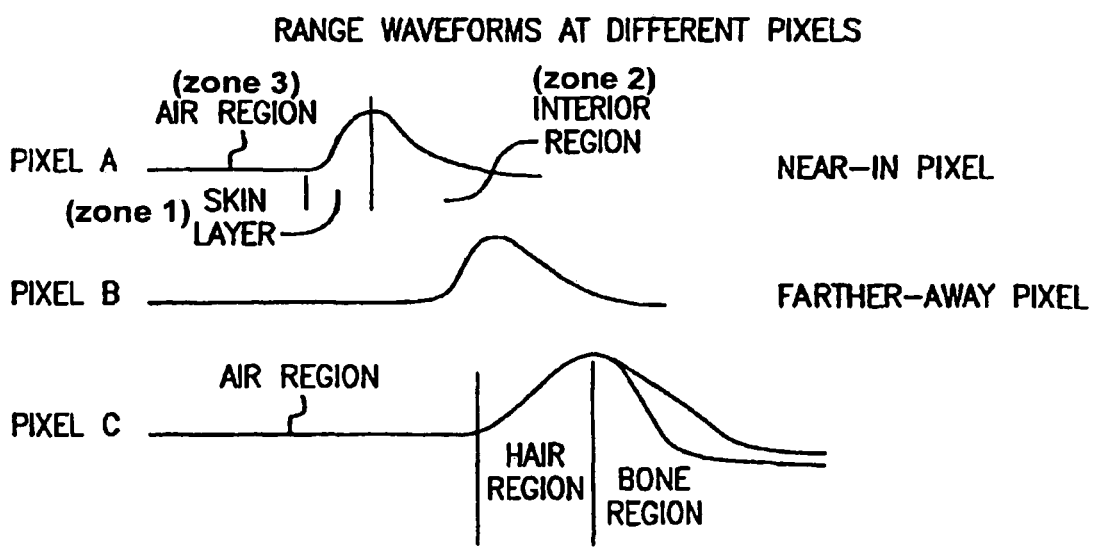
FIG. 3 is a triplet of range waveforms at different pixels—the (A), (B) and (C) portions representing returns from portions of a subject's anatomical features that are successively more remote from the transceiver.

Thus the graph in FIG. 3(A) represents pulse return from the air and the immediate interior of the patient's body, for a relatively near-in region of the anatomy e.g. a hand held just in front of the body, or the subject's nose or chin projecting forwardly of other parts of the body. Those in FIGS. 3(B) and (C) represent similar air and immediate-interior returns, but from progressively more-remote regions of the anatomy such as the throat.

Merely by way of example, in a scanning system these three returns might happen to be obtained in correspondence with the pulses a, b and c of FIG. 2, and therefore could represent different bodily features sighted at different vertical positions; or instead might instead happen to be sighted at different horizontal positions (pixels) along a common vertical position (pixel row).

In any event the interior regions (flesh behind skin, bone behind hair, etc.) depicted in the drawing are not merely distinguishable positionally, but also have respectively different characteristics. These different characteristics interact differently with a subject's stress.

Therefore they offer opportunities to normalize the readings, or to partially calibrate the apparatus on-the-fly, etc.—for further refinement of the resulting polygraphic data. For instance the laser-pulse reflectance of bone at a fixed, shallow depth within the body (e.g. at the forehead) is not likely to vary as a function of stress; therefore in suitable subjects (i.e. where a clear bone return is found) the software can form ratios of the nearer-in, skin reflectance signals with the bone reflectance, thereby enabling stabilization of those net signal components which represent conditions at the skin.

Such stabilization or normalization is not strictly necessary, using a well-calibrated active system. It might, however, be employed in such a way as to enable a less-stable operation, or a less finely calibrated or adjusted apparatus, or a slower computational regime, or combinations of these relaxations of operating demands and thereby to reduce the system cost or complexity.

The invention is readily practiced by straightforward modification of an existing laboratory lidar system for scanning. Calibration for the various parameters of interest is also straightforwardly obtained from breadboarding of optically fast detectors to measure amplitude and frequency shift in the scattered signal from a representative subject.

Figure 4A:
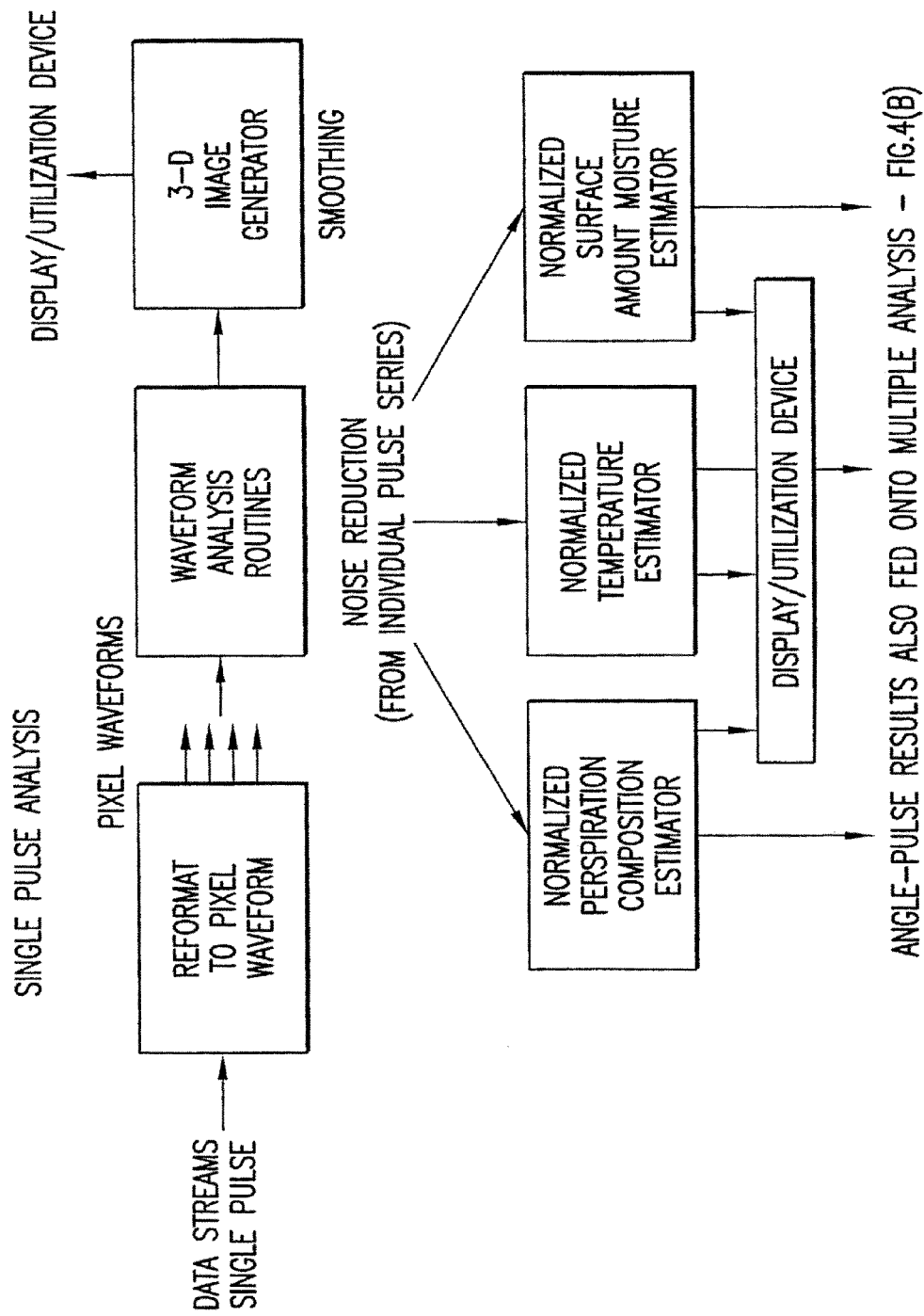
FIG. 4 is a pair of information-flow diagrams showing at (A) data derivation from a single lidar pulse, and at (B) data derivation from automatic analyses and comparisons of plural pulses considered as a set.
Figure 4B:
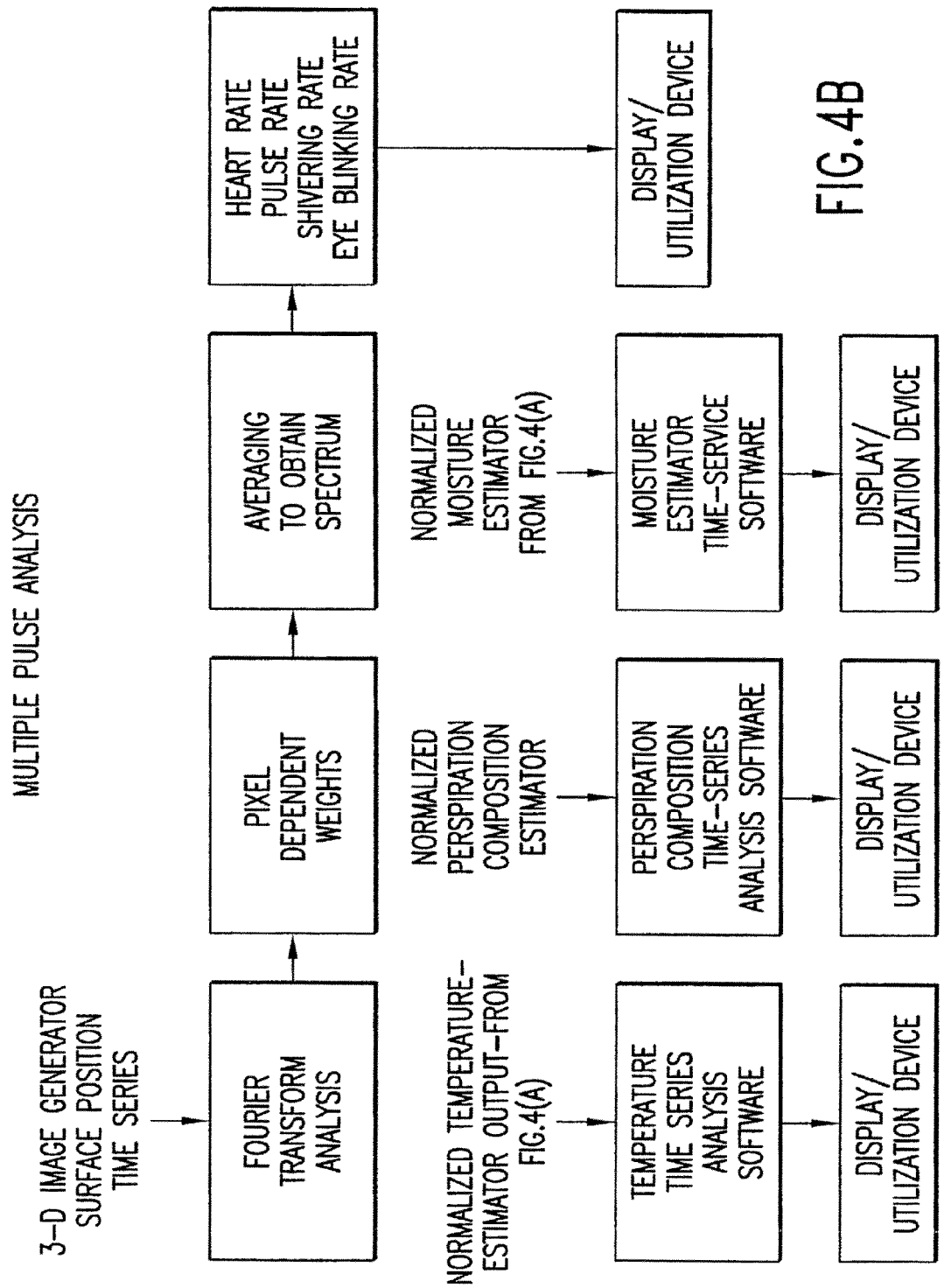
Figure 5:
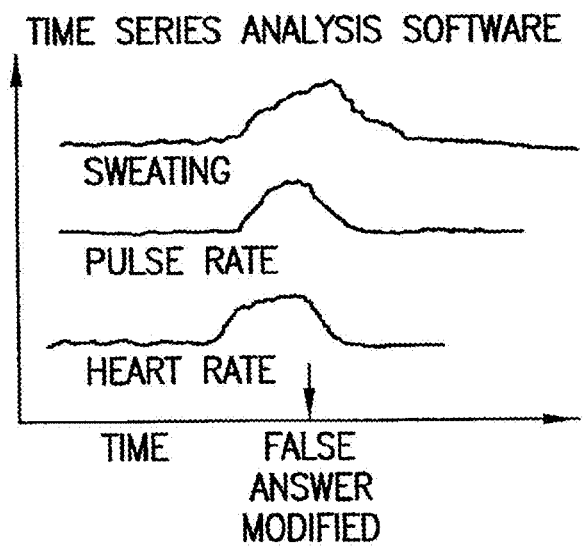
FIG. 5 is a comparative timing diagram showing plural graphs of vital-parameter excursion vs. time, as the basis of a simple time-series or coincidence analysis.
Figure 6:
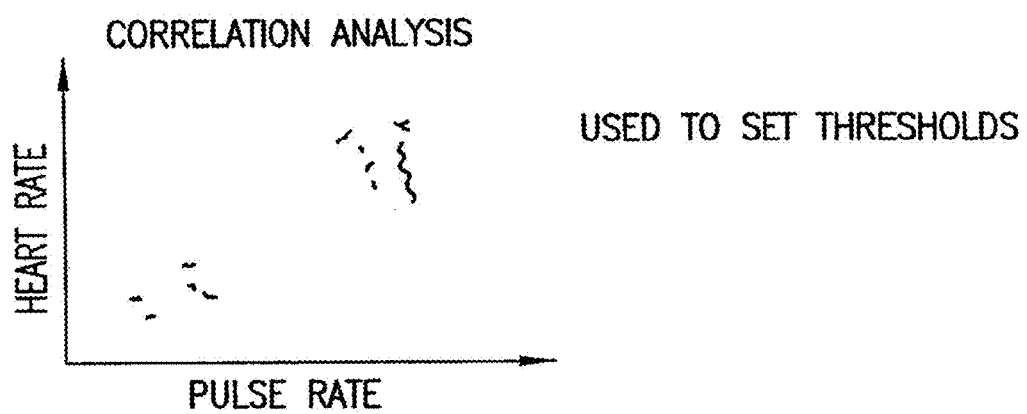
FIG. 6 is a graph of another data-evaluation approach that utilizes correlation as the basis of analysis.

A journeyman programmer should have no difficulty preparing simple data-acquisition control software to record the measurements. Analysis software is more extensive but well within the state of the art; it should plot and assess in near-real-time:

changes in amplitude, vs. time, of the reflected signal to determine changes in perspiration—such information being displayed after derivation from processing and comparison of individual pulses as detailed in FIG. 4(A), but with time-series (FIG. 5) or correlation (FIG. 6) analysis as well;

changes in carrier frequency—and subtended angle for the scattered signal, to establish small changes in body temperature—these variations too being developed from tracking of single pulses, as in FIG. 4(A); and fast Fourier transform of ongoing multipulse measurements to extract breathing and heart rates (and preferably some other periodic parameters, of interest, as mentioned earlier)—as represented in FIG. 4(B).

Further in regard to changes in carrier frequency, some helpful instrumental suggestions—but of course not at all directed to polygraphy—appear in a paper in the *Journal of the Korean Physical Society*, by Lee et al., entitled "LIDAR Measurement of Water Temperature by Using Frequency-Shifted Raman Scattering". (Lee's usage of the concept of frequency shift is literal, within the meaning of that term as introduced in the earlier "NOMENCLATURE" section of this document.) Another interesting piece of literature, mentioned in the Lee paper, is U.S. Pat. No. 4,123,160 issued to Caputo et al.

The application of Lee's reported work to the present invention is not for measuring the temperature in the ocean or other bodies of water (as described in the Lee paper); however, human beings and most other creatures are primarily made of water, and the shifted-Raman technique can be expected to carry across with minimal change. (Lee's development of Raman shifts, and of shifted-Raman technique, though perhaps not literally references to "frequency shift", is for purposes of this document also within the scope of the terminology "frequency shift" by virtue of the convention set forth in the "NOMENCLATURE" section of this document.)

Lee et al. discuss determining temperature sensitivity of bandwidth and shape in a lidar return. They describe a data-analysis technique for accomplishing this, particularly in the neighborhood of 30 C—i.e. near the body temperatures of humans and some other creatures. They describe measuring within one to two degrees, and suggest that there is no particular obstacle to making much finer measurements.

This technique depends on a shift in the return wavelength away from the transmitted wavelength—as suggested in the Applicants' original specification. The shift arises in nonlinear scattering by O—H bonds of the water molecule, or in other words interaction between the laser pulse and the molecules themselves.

Thus Lee et al. do not look at bandwidth of the return (Doppler broadening) at the transmitted frequency, but rather analyze Raman scattering at slightly offset frequencies. Such analysis, as explained, is straightforward and even patented for seawater (in the Caputo patent, mentioned above).

The same paper also teaches how to measure salt concentration by exploiting sensitivity of the Raman shift, in the return, to salt concentrations greater than 5% (page 661, penultimate paragraph). In the present invention this tactic can be used to refine detection and measurement of the living subject's perspiration.

A person of ordinary skill in this field will recognize, based upon the Applicants' above-mentioned suggestions and the related Lee paper and Caputo patent, that usable techniques involve determining amplitude of the return at the specific region of the return spectrum, in the Raman return band, and also noting its changes with concentration of salt content. These observations, easily automated, focus on the shift in central frequency and amplitude of this band.

The approach entails fitting this band in the return with a Gaussian spectral shape as prescribed by Lee et al. The same paper points out how polarization effects can be brought into the measurements at offset frequencies; incorporating polarization phenomena, in the context of the present invention, further expands the ability to determine perspiration and various other conditions of the body.

As previously mentioned, and as illustrated here, the FIG. 4 outputs are not limited to display but are also readily thresholded and directed to drive utilization means. The mathematics of Fourier analysis, as well as the statistical methodologies of time series (FIG. 5) or correlation (FIG. 6), are now found commercially in software modules that can be plugged into the analysis software to be developed here.

Hence these relatively sophisticated methods are available on an off-the-shelf basis for incorporation into practice of the present invention. As noted in FIG. 6, a zero-correlation (or if preferred a resting-correlation) value can be automatically developed from the same subject and applied to set thresholds for the thresholding operations mentioned earlier.

In a preferred embodiment, temperature resolution and update rate are 0.1° C. and 0.1 Hz respectively. Heart-rate resolution and update rate are roughly one beat/minute and 0.1 Hz respectively.

Although the principles of the invention should now be clear, any newly assembled prototype apparatus should be carefully validated by controlled tests on a series of subjects, and overall operation subjected to a carefully crafted, statistically valid blind test demonstration. In this regard it must be borne in mind that—even given reliable bioparameter data, whether obtained from the present invention or conventionally—polygraphy itself is not an exact science.

As mentioned earlier, some subjects inadvertently generate false positives; others deliberately generate false negatives or positives (or both) at will, degrading the reliability of all direct polygraphic systems and techniques. Conventional polygraphy provides little or no way to look behind the measurements, to determine whether observed reading patterns are arising in large part only from a subject's fear of the apparatus, or only from a subject's intentional, voluntarily screening of normal bodily responses—or are instead what they actually appear to be.

The present invention, however, does provide a way to look behind the superficial or apparent characteristics of the readings. It thereby offers several lie-detection advantages over conventional systems—particularly in that:

(a) a subject's responses can be assessed when the subject does not know the invention is in use; and furthermore (b) a subject's responses when the subject knows the invention is in use can now be compared with responses when the subject does not know;

(c) such comparisons thereby enable detection of an open or truthful subject's fear of the apparatus itself, and also to quantification of such a subject's unintended disruption of the polygraphic process;

(d) such comparisons also enable detection of a guarded or deceptive subject's ability to intentionally, voluntarily generate false positives or negatives, and also to quantification of that ability; and finally (d) such detection and quantification can lead in turn to some degree of cancellation of or compensation for the consequences of both (i) such unintended disruptions by a merely nervous subject, and (ii) such deceptive abilities on the part of a guarded subject.

In these several distinct ways the present invention can make very definite advances in the ability to deal with the problem of false positives and negatives in conventional polygraphy. Nevertheless, for a very conservative test, operation of the invention can be compared with that of conventional polygraphy as distinguished from any absolute measure of truthfulness in a wary or skillful subject.

By adapting and developing current IR lidar and detection technology, and standard fast Fourier transform algorithms, it is possible to measure changes in a subject's breathing, perspiration, heartbeat, blinking, shivering and temperature several times a second without physical contact—and if desired without alerting the subject, whether during detention or during structured interviews. This capability must be tempered with due regard for applicable privacy rights and other applicable civil rights of the subject.

It will be understood that the foregoing disclosure is intended to be merely exemplary, and not to limit the scope of the invention.

What is claimed is:

1. A system for noninvasively conducting polygraphic tests for determining the existence of stress on a living subject; said system comprising:
   a lidar radiation transmitter for transmitting a plurality of coherent lidar radiation pulses, in a particular optical frequency band that serves as a lidar data carrier;
   a lidar receiver for receiving returned lidar pulses from the subject, wherein between said transmitted and received pulses, respectively, there is a variable time delay that is associated with variable distances between the subject and the transmitter and receiver;
   said received pulses with variable delay containing information relating to a plurality of physiological characteristics of the subject indicative of stress of the subject;
   means for time-resolving each received pulse to analyze the delay and thereby the variable distances;
   an information-processing device in communication with said receiver for processing said variable time delay; and
   means for measuring frequency shifts in the carrier of said received pulses, which are a measure of the temperature of the subject.

2. The system of claim 1, wherein:
   said information-processing device also interprets said measured frequency shifts in the carrier of said received radiation pulses to determine the temperature of the subject.

3. The system of claim 2, wherein said time-resolving means comprise:
   means for determining relative distance from the transmitter to the subject and thence to said receiver.

4. The system of claim 3, wherein:
   said information-processing device utilizes a fast Fourier transform of a series of returned radiation pulses to measure respiration rate or heart rate, or both, of the subject.

5. The system of claim 1, further comprising:
   a display device for displaying an output of said plurality of physiological characteristics.

6. The system of claim 5, wherein:
   said plurality of characteristics displayed by said display device includes at least one of the subject's respiration rate and heart rate, in addition to said temperature.

7. The system of claim 5, wherein:
   the information-processing device combines the plurality of physiological characteristics to produce a further single output, displayed on said display device, indicative of the truthfulness of the subject.

8. The system of claim 5, wherein:
   said plurality of physiological characteristics includes:
   the subject's perspiration, or
   salinity on or in the subject, or
   both perspiration and said salinity; and
   said information-processing device includes a spectral analysis device for determining;
      the existence and degree of perspiration on the subject's body, and
      the existence and magnitude of salinity on or in the subject, or
      both.

9. The system of claim 8, wherein:
   said information-processing device measures changes in amplitude versus time of said reflected pulses to measure perspiration of the subject.

10. The system of claim 1, wherein:
    the transmitter comprises means for transmitting said plurality of lidar pulses as a substantially unitary single sequence of multiple lidar pulses; and
    said substantially unitary single sequence of lidar pulses generates data indicative of substantially all of said plurality of physiological characteristics.

11. The system of claim 1, wherein:
    said transmitter produces a plurality of lidar radiation pulses that are progressively shifted over at least a portion of the subject's body.

12. The system of claim 1, wherein:
    said transmitter produces a plurality of lidar pulses, all of which are directed toward the subject's body; and
    the said information-processing device includes an image remapper.

13. The system of claim 1, wherein:
    said receiver in general receives lidar pulses returned from:
       within the subject's body, and
       gas or vapor if present outside the subject's body, as well as
       the surface of the subject's body; and
    the information-processing device comprises:
       means for applying said processed variable time delay to discriminate among these three types of received return, and
       means for applying different algorithms to analyze the three types of return, respectively.

14. A method for noninvasively conducting polygraphic tests for assessing existence or degree of stress on a living subject; said method comprising the steps of:
    producing a substantially single, unitary series of coherent lidar-radiation pulses, from a lidar transmitter that is at a distance from the subject;
    transmitting said series of coherent radiation pulses toward the subject;
    receiving the substantially single, unitary series of lidar pulses, returned from the subject, by a receiver that is at a distance from the subject, said received pulses including, relative to the transmitted pulses, a measurable frequency shift; and
    analyzing said measurable frequency shift, to determine various physiological characteristics of the subject which are indicative of stress of the subject;

wherein substantially all of said various physical characteristics are determined from said substantially single, unitary series of lidar pulses; and wherein said receiving step comprises receiving lidar pulses of different types, namely returned at least from (1) within the subject's body, and (2) the surface of the subject's body; and the analyzing step comprises:

applying information about arrival times of the received lidar pulses to discriminate among different types of received return, and applying different algorithms for analyzing the said different types of received return, respectively.

15. The method of claim 14:

further comprising the step of interrogating the human subject during the producing, transmitting and receiving steps; and wherein the receiving step further comprises receiving lidar pulses returned from gas or vapor if present outside the subject's body.

16. A system for noninvasively conducting polygraphic tests to determine existence of stress on a living subject; said system comprising:

a lidar transmitter for transmitting a plurality of coherent lidar pulses, in a particular frequency band that serves as a lidar-data carrier;

a lidar receiver for receiving returned pulses returned from the subject, wherein between the transmitted and received pulses, respectively, there is at least one measurable frequency shift in the carrier;

the at least one measurable frequency shift containing information relating to plural physiological characteristics, of the living subject, indicative of stress of the subject;

means for time-resolving each received pulse;

wherein the time-resolving means comprise means for measuring frequency shifts in the carrier of said received pulses, and wherein the shifts are a measure of the temperature of the subject; and an information-processing device in communication with said receiver for processing said at least one measurable frequency shift.

17. The system of claim 16, wherein:

said received pulses further include, relative to the transmitted pulses, a variable time delay relative to the transmitted pulses; and the receiver further comprises means for analyzing said time delay, to determine at least one physiological characteristic of the subject which is indicative of stress of the subject or truthfulness of the subject, or both.

18. The system of claim 17, wherein:

the lidar transmitter comprises plural laser emitters operating at respective frequencies;

the frequencies are at least slightly different from one another;

the plural laser emitters are directed toward respective points, of the subject's body;

the receiving means in general comprise means for receiving pulses of different types, namely pulses returned at least from (1) within the subject's body, and from (2) the surface of the subject's body; and the analyzing means comprise means for:

applying said analyzed variable time delay to discriminate between or among different types of received return, and applying different algorithms to analyze the different types of return, respectively.

19. The system of claim 18, wherein:

said points of the subjects body are at least slightly different from one another;

the receiving means further comprise means for:

receiving pulses due to the plural laser emitters, respectively, and receiving pulses of a third type, namely pulses returned from gas or vapor if present outside the subject's body;

the analyzing means also comprise means for:

applying a further different algorithm to analyze the third type of return, deriving respective information from pulses received due to the plural laser emitters, and combining information derived from received pulses due to the plural laser emitters, respectively, to generate enhanced information.

* * * * *